United States Patent
Manneck et al.

(10) Patent No.: US 9,980,891 B2
(45) Date of Patent: *May 29, 2018

(54) AGENT AND METHOD FOR OXIDATIVE HAIR COLORING OR BLEACHING, WHICH ARE GENTLE ON HAIR

(71) Applicant: Henkel AG & Co. KGaA, Duesseldorf (DE)

(72) Inventors: Hartmut Manneck, Barnitz (DE); Thomas Hippe, Appen (DE); Astrid Kleen-Fehres, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/352,814

(22) Filed: Nov. 16, 2016

(65) Prior Publication Data

US 2017/0181946 A1    Jun. 29, 2017

Related U.S. Application Data

(60) Provisional application No. 62/345,085, filed on Jun. 3, 2016.

(30) Foreign Application Priority Data

Nov. 20, 2015 (DE) .................. 10 2015 222 946
May 31, 2016 (DE) .................. 10 2016 209 468

(51) Int. Cl.

| | | |
|---|---|---|
| *A61Q 5/10* | (2006.01) |
| *A61K 8/44* | (2006.01) |
| *A61K 8/22* | (2006.01) |
| *A61Q 5/08* | (2006.01) |
| *A61K 8/36* | (2006.01) |
| *A61K 8/362* | (2006.01) |
| *A61K 8/19* | (2006.01) |
| *A61K 8/25* | (2006.01) |
| *A61K 8/41* | (2006.01) |

(52) U.S. Cl.
CPC ............... *A61K 8/447* (2013.01); *A61K 8/19* (2013.01); *A61K 8/22* (2013.01); *A61K 8/25* (2013.01); *A61K 8/36* (2013.01); *A61K 8/362* (2013.01); *A61K 8/41* (2013.01); *A61K 8/44* (2013.01); *A61Q 5/08* (2013.01); *A61Q 5/10* (2013.01); *A61K 2800/4324* (2013.01); *A61K 2800/882* (2013.01)

(58) Field of Classification Search
CPC . A61K 8/447; A61K 8/22; A61K 8/36; A61K 8/362; A61K 8/19; A61K 8/25; A61K 8/41; A61K 8/44; A61K 2800/4324; A61K 2800/882; A61Q 5/10; A61Q 5/08
USPC .......................................................... 8/405
See application file for complete search history.

(56) References Cited

U.S. PATENT DOCUMENTS

| | | | | |
|---|---|---|---|---|
| 5,030,241 | A * | 7/1991 | Clausen | A61K 8/418 564/441 |
| 2002/0189034 | A1* | 12/2002 | Kitabata | A61K 8/19 8/405 |
| 2008/0262085 | A1 | 10/2008 | Kainz et al. | |
| 2015/0053228 | A1* | 2/2015 | Bonauer | A45D 19/0008 132/208 |

FOREIGN PATENT DOCUMENTS

| | | |
|---|---|---|
| DE | 10051774 A1 | 4/2002 |
| EP | 1174112 A2 | 1/2002 |

OTHER PUBLICATIONS

STIC Search Report dated Mar. 23, 2017.*
English Abstract (May 19, 2017) of the Japanese Patent No. 2006273782 A.*

* cited by examiner

*Primary Examiner* — Eisa B Elhilo
(74) *Attorney, Agent, or Firm* — James J. Cummings

(57) ABSTRACT

An agent for oxidative hair coloring or bleaching, which is gentle on the hair, and a gentle method for oxidative hair coloring or bleaching, in which keratin fibers are protected against oxidative effects.

21 Claims, No Drawings

AGENT AND METHOD FOR OXIDATIVE HAIR COLORING OR BLEACHING, WHICH ARE GENTLE ON HAIR

FIELD OF THE INVENTION

The present invention generally relates to an agent for oxidative hair coloring or bleaching which is gentle on the hair, and to a gentle method for oxidative hair coloring or bleaching, in which keratin fibers are protected against oxidative effects and/or oxidative hair damage is repaired.

BACKGROUND OF THE INVENTION

During the oxidative coloring or bleaching of hair, the problem arises that damage to the keratin fibers may occur due to the aggressive agents. In particular, the natural hydrophobicity of the keratin fibers is reduced since the coloring or lightening agents must first make the hair penetrable in order to take effect. On the one hand, however, the water-repelling effect is a natural mode of protection for the hair, and on the other hand parameters desired by the consumer, such as shine, suppleness, feel and "fall" of the hair, are closely linked thereto.

In order to overcome the aforementioned disadvantages, so-called pretreatment agents are available on the market, which are said to protect the hair against the aggressive effect. However, said pretreatment agents often weigh down the hair or adversely affect the outcome of the subsequent lightening or coloring of the hair. In particular, the wash fastness of the coloring may be worsened by the pretreatment agent. Also known are numerous aftertreatment agents which attempt to repair the damage to the hair that is caused during the oxidative coloring treatment. However, all of these methods require a multistage application process, specifically the need to apply a further hair treatment agent either before or after the coloring operation. This is often perceived as bothersome by the consumer, since already the oxidative coloring treatment itself, which involves multiple operating steps and a leave-in time of up to 60 minutes, is very time-consuming.

It is therefore desirable to provide an agent and a method for oxidative hair coloring by way of a hair-protecting treatment, which overcomes the aforementioned disadvantages without having a negative effect on the color as a result from the oxidative coloring treatment. In particular, it is desirable to provide a coloring agent and a method by which the hair is not weighed down and as little damage to the hair as possible occurs. It is further desirable for the hair protection achieved to take as little time as possible and to take place to the extent possible together with the coloring step itself.

The use of dicarboxylic acids such as succinic acid in hair care is prior art. These are widely used in shampoos and particularly in conditioners, in order to provide a caring effect. For instance, patent application WO 2005/115314 A1 discloses a method for restructuring keratin fibers, in which the keratin fibers are brought into contact with cystine and with at least one dicarboxylic acid having 2 to 10 carbon atoms, wherein preferred dicarboxylic acids are selected from oxalic acid, malonic acid, succinic acid, glutaric acid, adipic acid, pimelic acid, azelaic acid, maleic acid, fumaric acid and sorbic acid, and particular preference is given to succinic acid. Patent application DE 10051774 A1 describes the use of short-chain carboxylic acids having a molecular weight of less than 750 g/mol in cosmetic agents as an active substance for restructuring keratin fibers. Patent application EP 1174112 A discloses hair treatment agents which, besides an organic acid, includes as further mandatory constituents an organic solvent, a cationic surfactant and a higher alcohol, and serve for repairing pores in hair.

Desirable features and characteristics of the present invention will become apparent also in view of the subsequent detailed description of the invention and the appended claims, taken in conjunction with this background of the invention.

BRIEF SUMMARY OF THE INVENTION

An oxidative coloring or bleaching agent for keratin fibers, in particular for human hair, includes: a) at least one saturated dicarboxylic acid having 2 to 10 carbon atoms and/or at least one salt of said acid(s); b) at least one amino acid of formula (VI)

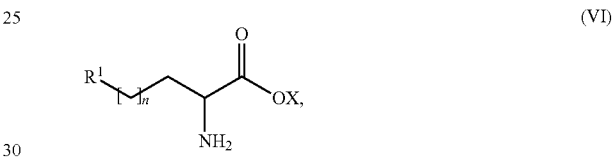

(VI)

in which X represents a hydrogen atom or a monovalent or divalent cation; n represents zero, 1, 2 or 3; $R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid; c) also at least one alkalizing agent, selected from ammonium hydroxide, monoethanolamine and sodium silicates, and mixtures thereof; d) optionally at least one oxidation dye precursor and/or at least one substantive dye; e) water; and f) at least one peroxide compound.

A method for the oxidative coloring and/or lightening of keratin fibers, in particular of human hair, includes the following method steps: I. providing a composition (A), including a) at least one saturated dicarboxylic acid having 2 to 10 carbon atoms and/or at least one salt of said acid(s); b) at least one amino acid of formula (VI)

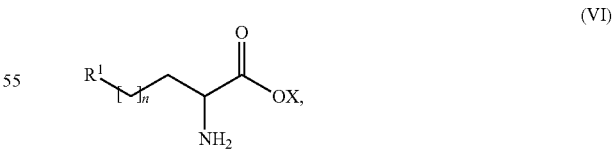

(VI)

in which X represents a hydrogen atom or a monovalent or divalent cation; n represents zero, 1, 2 or 3; $R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid; c) water; and d) optionally also at least one substance selected from compounds of general formula (III)

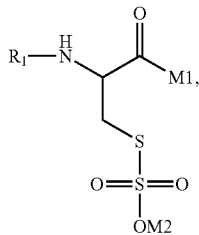

(III)

wherein R1 represents a hydrogen atom or a structural element of formula (IV)

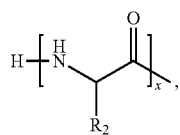

(IV)

wherein x represents an integer from 1 to 100; the radical R2 in each of the structural elements of formula (IV) can in each case be selected independently of the preceding structural element of formula (IV); R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group; M1 represents the group —OM2 or a structural element of formula (V)

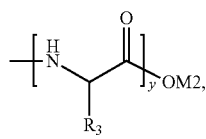

(V)

wherein y represents an integer from 1 to 100; the radical R3 in each of the structural elements of formula (V) can in each case be selected independently of the preceding structural element of formula (V); R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group; M2 represents a hydrogen atom, an equivalent of a monovalent or polyvalent cation or an ammonium ion ($NH_4^+$); and polymers A which have at least ten constituent units of formula (I)

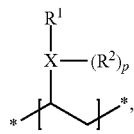

(I)

in which X represents nitrogen or oxygen and $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and p=0 when X represents oxygen and p=1 when X represents nitrogen, the polymer A including no permanently ionic constituent units, wherein the composition (A) preferably has a pH in the range from 3.5 to 7.1, preferably 4.5 to 6.5, particularly preferably 5.0 to 6.0, in each case measured at 20° C.; II. providing a composition (B), including e) at least one alkalizing agent, selected from ammonium hydroxide, monoethanolamine and sodium silicates, and mixtures thereof; f) optionally water; and g) optionally at least one oxidation dye precursor and/or at least one substantive dye, wherein the composition (B) preferably has a pH in the range from 6.5 to 11.0, preferably 8 to 10.5, particularly preferably 8.5 to 10.0, in each case measured at 20° C.; III. providing a composition (C), including h) at least one peroxide compound, which is preferably hydrogen peroxide, wherein the composition (C) preferably has a pH in the range from 2.5 to 6.5, preferably 3.0 to 5.5, particularly preferably 3.5 to 5.0, in each case measured at 20° C.; IV. mixing compositions (A), (B) and (C) with one another, then immediately; V. applying the mixture of (A), (B) and (C) to the keratin fibers, in particular to the human hair; VI. rinsing out after a leave-in time of 0.1 to 60 minutes, preferably 1 to 45 minutes, particularly preferably 10 to 30 minutes; and VII. optionally further hair treatments, such as styling, conditioning and/or drying.

A composition (A) includes at least one saturated dicarboxylic acid having 2 to 10 carbon atoms in a total amount of 2 to 20% by weight, preferably 5 to 15% by weight, particularly preferably 8 to 12% by weight, in each case converted to the undissociated dicarboxylic acid and based on the weight of the composition (A), the dicarboxylic acid preferably being selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, particular preference being given to succinic acid and malic acid and extreme preference being given to succinic acid; and at least one amino acid of formula (VI) and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), wherein preferably at least one of the amino acids arginine, histidine or lysine and/or a salt thereof is included in a total amount of 0.4 to 7.0% by weight, preferably 0.8 to 5.0% by weight, particularly preferably 1.5 to 4.0% by weight, in each case converted to the undissociated amino acid and based on the weight of the composition (A); and water, preferably in an amount of 50 to 92% by weight, particularly preferably 60 to 87% by weight and extremely preferably 65 to 80% by weight, in each case based on the weight of the composition (A); optionally also at least one polymer A which has at least ten constituent units of formula (I)

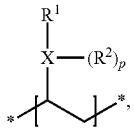

(I)

in which X represents nitrogen or oxygen and $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and p=0 when X represents oxygen and p=1 when X represents nitrogen, the polymer A including no permanently ionic constituent units, wherein preferably the at least one polymer A is included in a total amount of 0.5 to 14% by weight, preferably 1.0 to 11% by weight, particularly preferably 2.0 to 10% by weight, in each case based on the weight of the composition (A), wherein the composition (A) preferably has a pH in the range from 3.5 to 7.1, preferably 4.5 to 6.5, particularly preferably 5.0 to 6.0, in each case measured at 20° C.

A method for the oxidative coloring and/or lightening of keratin fibers, in particular of human hair, includes the following method steps: I. providing a composition (AB), including a) at least one saturated dicarboxylic acid having 2 to 10 carbon atoms and/or at least one salt of said acid(s); b) at least one amino acid of formula (VI)

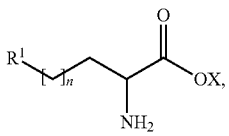

(VI)

in which X represents a hydrogen atom or a monovalent or divalent cation; n represents zero, 1, 2 or 3; $R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid; the amino acid of formula (VI) preferably being selected from arginine, lysine, histidine and mixtures thereof, particularly preferably mixtures of arginine and lysine, or at least one salt of said amino acids; c) optionally also at least one substance selected from compounds of general formula (III)

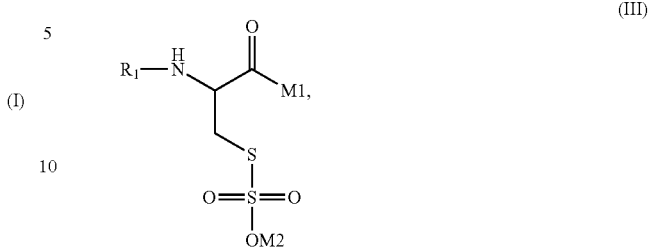

(III)

wherein R1 represents a hydrogen atom or a structural element of formula (IV)

(IV)

wherein x represents an integer from 1 to 100; the radical R2 in each of the structural elements of formula (IV) can in each case be selected independently of the preceding structural element of formula (IV); R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group; M1 represents the group —OM2 or a structural element of formula (V)

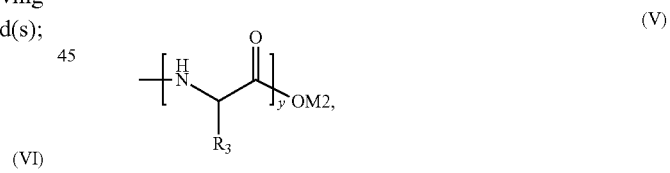

(V)

wherein y represents an integer from 1 to 100; the radical R3 in each of the structural elements of formula (V) can in each case be selected independently of the preceding structural element of formula (V); R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group; M2 represents a hydrogen atom, an equivalent of a monovalent or polyvalent cation or an ammonium ion ($NH_4$)$^+$; and polymers A which have at least ten constituent units of formula (I)

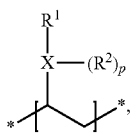

(I)

in which X represents nitrogen or oxygen and $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and p=0 when X represents oxygen and p=1 when X represents nitrogen; the polymer A including no permanently ionic constituent units; d) at least one alkalizing agent, selected from ammonium hydroxide, monoethanolamine and sodium silicates, and mixtures thereof; e) water; and f) optionally at least one oxidation dye precursor and/or at least one substantive dye; II. providing a composition (C), including g) at least one peroxide compound, which is preferably hydrogen peroxide; III. mixing compositions (AB) and (C) with one another, then immediately; IV. applying the mixture of (AB) and (C) to the keratin fibers, in particular to the human hair; V. rinsing out after a leave-in time of 0.1 to 60 minutes, preferably 1 to 45 minutes, particularly preferably 10 to 30 minutes; and VI. optionally further hair treatments, such as styling, conditioning and/or drying.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that oxidative coloring and bleaching agents which includes at least one saturated dicarboxylic acid having 2 to 10 carbon atoms and at least one amino acid of formula (VI) in addition to typical constituents such as water, ammonium hydroxide and/or monoethanolamine as alkalizing agents and a peroxide compound, such as hydrogen peroxide, lead to considerably improved hair protection during the oxidative hair treatment, without adversely affecting the results of the oxidative coloring or bleaching treatment. It has surprisingly been found that, due to the content of at least one saturated dicarboxylic acid having 2 to 10 carbon atoms in combination with at least one amino acid of formula (VI), the hair during the coloring and/or lightening process is protected against damage caused by the high pH of the agent and by the oxidizing agent. This is clear inter alia from the fact that less hair breakage occurs during subsequent combing and hair loses less elasticity, as can be demonstrated by tensile strength measurements, than after applying coloring and bleaching agents which are not in accordance with the invention.

In a first embodiment, the subject matter of the present invention is an oxidative coloring or bleaching agent for keratin fibers, in particular for human hair, including
a) at least one saturated dicarboxylic acid having 2 to 10 carbon atoms and/or at least one salt of said acid(s),
b) at least one amino acid of formula (VI)

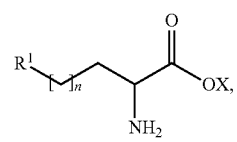

(VI)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
c) also at least one alkalizing agent, selected from ammonium hydroxide, monoethanolamine and sodium silicates, and mixtures thereof,
d) optionally at least one oxidation dye precursor and/or at least one substantive dye,
e) water, and
f) at least one peroxide compound.

Another subject matter of the present invention is a method for the oxidative coloring and/or lightening of keratin fibers, in particular of human hair, in which a coloring or bleaching agent is applied to the keratin fibers, in particular to the human hair, and is rinsed out again after a leave-in time of 0.1 to 60 minutes, preferably 1 to 45 minutes, particularly preferably 10 to 30 minutes, said coloring or bleaching agent including
a) at least one saturated dicarboxylic acid having 2 to 10 carbon atoms and/or at least one salt of said acid(s),
b) at least one amino acid of formula (VI)

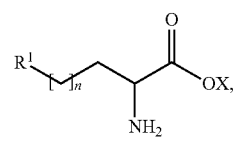

(VI)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
c) also at least one alkalizing agent, selected from ammonium hydroxide, monoethanolamine and sodium silicates, and mixtures thereof,
d) optionally at least one oxidation dye precursor and/or at least one substantive dye,
e) water, and
f) at least one peroxide compound.

Another subject matter of the present invention is a method for the oxidative coloring and/or lightening of keratin fibers, in particular of human hair, which includes the following method steps:

I. providing a composition (A), including
   a) at least one saturated dicarboxylic acid having 2 to 10 carbon atoms and/or at least one salt of said acid(s),
   b) at least one amino acid of formula (VI)

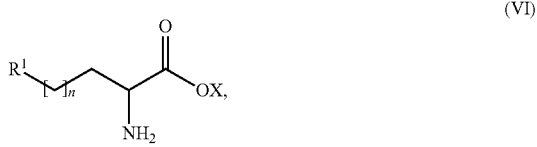

(VI)

in which
   X represents a hydrogen atom or a monovalent or divalent cation;
   n represents zero, 1, 2 or 3;
   $R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
   c) water, and
   d) optionally also at least one substance selected from compounds of general formula (III)

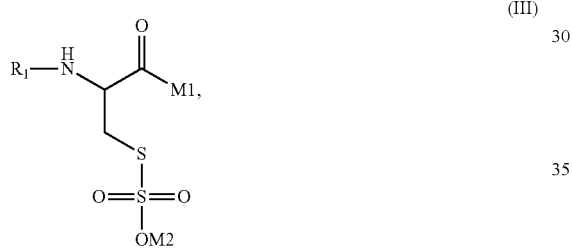

(III)

wherein
   R1 represents a hydrogen atom or a structural element of formula (IV)

(IV)

wherein
   x represents an integer from 1 to 100,
   the radical R2 in each of the structural elements of formula (IV) can in each case be selected independently of the preceding structural element of formula (IV),
   R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-yl-methyl group, a 1H-indol-3-ylmethyl group or a (sulfosulfanyl)methyl group,
   M1 represents the group —OM2 or a structural element of formula (V)

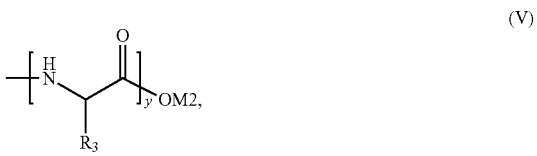

(V)

wherein
   y represents an integer from 1 to 100,
   the radical R3 in each of the structural elements of formula (V) can in each case be selected independently of the preceding structural element of formula (V),
   R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-yl-methyl group, a 1H-indol-3-ylmethyl group or a (sulfosulfanyl)methyl group,
   M2 represents a hydrogen atom, an equivalent of a monovalent or polyvalent cation or an ammonium ion $(NH_4)^+$, and
   polymers A which have at least ten constituent units of formula (I)

(I)

in which
   X represents nitrogen or oxygen and
   —$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
   p=0 when X represents oxygen and p=1 when X represents nitrogen,
   the polymer A including no permanently ionic constituent units,
II. providing a composition (B), including
   e) at least one alkalizing agent, selected from ammonium hydroxide, monoethanolamine and sodium silicates, and mixtures thereof,
   f) optionally water, and
   g) optionally at least one oxidation dye precursor and/or at least one substantive dye, III. providing a composition (C), including
   h) at least one peroxide compound, which is preferably hydrogen peroxide,
IV. mixing compositions (A), (B) and (C) with one another, then immediately
V. applying the mixture of (A), (B) and (C) to the keratin fibers, in particular to the human hair, and
VI. rinsing out after a leave-in time of 0.1 to 60 minutes, preferably 1 to 45 minutes, particularly preferably 10 to 30 minutes,
VII. optionally further hair treatments, such as styling, conditioning and/or drying.

Another subject matter of the present invention is a method for the oxidative coloring and/or lightening of keratin fibers, in particular of human hair, which includes the following method steps:
I. providing a composition (AB), including
   a) at least one saturated dicarboxylic acid having 2 to 10 carbon atoms and/or at least one salt of said acid(s),
   b) at least one amino acid of formula (VI)

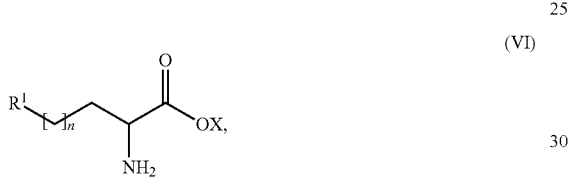

(VI)

in which

X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
the amino acid of formula (VI) preferably being selected from arginine, lysine, histidine and mixtures thereof, particularly preferably mixtures of arginine and lysine, or at least one salt of said amino acids,
   c) optionally also at least one substance selected from compounds of general formula (III)

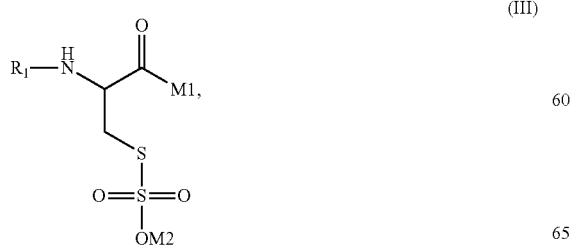

(III)

wherein
R1 represents a hydrogen atom or a structural element of formula (IV)

(IV)

wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

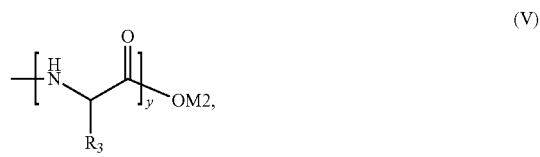

(V)

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$, and
polymers A which have at least ten constituent units of formula (I)

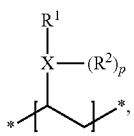

(I)

in which
- X represents nitrogen or oxygen and
- $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
- p=0 when X represents oxygen and p=1 when X represents nitrogen, the polymer A including no permanently ionic constituent units, d) at least one alkalizing agent, selected from ammonium hydroxide, monoethanolamine and sodium silicates, and mixtures thereof, e) water, and f) optionally at least one oxidation dye precursor and/or at least one substantive dye, II. providing a composition (C), including
  g) at least one peroxide compound, which is preferably hydrogen peroxide, III. mixing compositions (AB) and (C) with one another, then immediately IV. applying the mixture of (AB) and (C) to the keratin fibers, in particular to the human hair, and V. rinsing out after a leave-in time of 0.1 to 60 minutes, preferably 1 to 45 minutes, particularly preferably 10 to 30 minutes, VI. optionally further hair treatments, such as styling, conditioning and/or drying.

Saturated Dicarboxylic Acids Having 2 to 10 Carbon Atoms and/or at Least One Salt of Said Acid(s)

Saturated dicarboxylic acids having 2 to 10 carbon atoms which are preferred according to the invention are selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids. Succinic acid and malic acid are particularly preferred according to the invention. Succinic acid is particularly preferred. Said dicarboxylic acids significantly help to reduce the damage to the hair that is brought about by the coloring or bleaching agents according to the invention.

Depending on the pH of the coloring or bleaching agent according to the invention or of the compositions (A) or (AB) used in one of the coloring or bleaching methods according to the invention, the at least one saturated dicarboxylic acid having 2 to 10 carbon atoms may be in the form of an undissociated acid or in partially dissociated or completely dissociated form. If the at least one saturated dicarboxylic acid having 2 to 10 carbon atoms is in partially dissociated or completely dissociated form, the counter-ion is selected from physiologically acceptable cations, such as in particular the alkali metal, alkaline earth metal and zinc ions as well as ammonium ions, alkylammonium ions, alkanolammonium ions and glucammonium ions, in particular the mono-, di- and trimethyl-, -ethyl- and -hydroxyethyl ammonium ions. Preference is also given to the salts of the saturated dicarboxylic acids having 2 to 10 carbon atoms with amino-$C_1$-$C_6$-alkanols, in particular with monoethanolamine, and amino-$C_1$-$C_6$-alkanediols, in particular with 2-amino-2-methyl-1-propanol, 2-amino-2-methyl-1,3-propanediol, 2-amino-1-propanol, 3-amino-1-propanol, 1-amino-2-propanol (MIPA) and 2-amino-2-(hydroxymethyl)-1,3-propanediol (TRIS), particular preference being given to the salts with monoethanolamine, 2-amino-2-methyl-1-propanol and 2-amino-2-methyl-1,3-propanediol.

Sodium, potassium, magnesium, ammonium and monoethanol ammonium ions are extremely preferred as counter-ions for the partially or completely dissociated saturated dicarboxylic acids having 2 to 10 carbon atoms. Besides these, however, use may also be made of saturated dicarboxylic acids which have 2 to 10 carbon atoms and which are neutralized with alkaline-reacting amino acids, such as for example arginine, lysine, ornithine and histidine.

The sodium, potassium, ammonium, monoethanolammonium, lysine and arginine salts and mixtures thereof are preferred salts of the saturated dicarboxylic acids having 2 to 10 carbon atoms.

Preferred coloring or bleaching agents according to the invention includes the at least one saturated dicarboxylic acid having 2 to 10 carbon atoms or one or more salts thereof in a total amount of 0.2 to 4% by weight, preferably 0.33 to 3% by weight, particularly preferably 0.5 to 2% by weight, in each case converted to the undissociated dicarboxylic acid and based on the weight of the coloring or bleaching agent.

Even when the dicarboxylic acids are present in salt form, the amounts specified above relate to the respective dicarboxylic acid in undissociated form, so as not to falsify the stated amounts due to different molecular weights of the salts. For example, an initial sample weight of 15% by weight disodium succinate hexahydrate would give, when converted, a succinic acid concentration of 6.55% by weight.

Amino Acid of Formula (VI)

The reduced hair-damaging effect of the coloring or bleaching agent according to the invention can be largely attributed to the aforementioned dicarboxylic acids in collaboration with at least one selected amino acid of formula (VI).

The coloring or bleaching agents according to the invention therefore includes as a further obligatory component at least one amino acid of formula (VI)

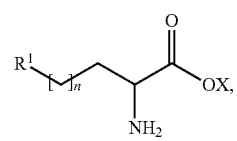

(VI)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid.

Preferred amino acids of formula (VI) are selected from arginine, lysine, histidine, asparagine, glutamine, cysteine, methionine, tryptophan and mixtures thereof. Particularly preferred coloring or bleaching agents includes mixtures of arginine and lysine or at least one salt of said amino acids.

Preferred coloring or bleaching agents according to the invention includes the at least one amino acid of formula (VI) or one or more salts thereof in a total amount of 0.05 to 3% by weight, preferably 0.1 to 2% by weight, particularly preferably 0.2 to 1.2% by weight, in each case converted to the undissociated amino acid and based on the weight of the coloring or bleaching agent.

Further particularly preferred coloring or bleaching agents according to the invention includes mixtures of arginine and lysine or at least one salt of said amino acids in a total amount of 0.05 to 3% by weight, preferably 0.1 to 2% by weight, particularly preferably 0.2 to 1.2% by weight, in each case converted to the undissociated acid and based on the weight of the coloring or bleaching agent.

Alkalizing Agent

The coloring or bleaching agents according to the invention also includes at least one alkalizing agent, selected from ammonium hydroxide, monoethanolamine and sodium silicates, and mixtures thereof.

In order to achieve the desired long-lasting coloring or lightening of the keratin fibers, the coloring or bleaching agent according to the invention must have a pH in the range from 6.5 to 11.0, preferably 8 to 10.5, particularly preferably 8.5 to 10, in each case measured at 20° C. At these pH values, the outer keratin fiber layer opens optimally to absorb the oxidation dye precursors, and the desired effect of the peroxide compound is optimally achieved.

With preference, ammonia is used in the form of its aqueous solution. Suitable aqueous ammonia solutions may be 10 to 35% strength solutions (calculated in % by weight, 100 g aqueous ammonia solution thus includes 10 to 35 g ammonia). Preferably, ammonia is used in the form of a 20 to 30% strength by weight solution, particularly preferably in the form of a 25% strength by weight solution.

In one particularly preferred embodiment, the coloring or bleaching agent according to the invention is characterized in that it includes ammonium hydroxide in an amount of 0.20 to 2.5% by weight, preferably 0.5 to 2.0% by weight, more preferably 1.0 to 1.5% by weight and particularly preferably 0.31 to 0.8% by weight, based on the total weight of the coloring or bleaching agent according to the invention.

Preferred coloring or bleaching agents according to the invention includes monoethanolamine in addition to or instead of ammonium hydroxide.

In order to achieve maximum odor masking and in order to optimize the fastness properties, monoethanolamine is included in a total amount of 0.2 to 6.5% by weight, preferably 0.5 to 4.0% by weight, more preferably 0.7 to 2.5% by weight and particularly preferably 0.8 to 1.6% by weight, based on the total weight of the coloring or bleaching agent according to the invention.

In the context of the present invention, sodium silicates are chemical compounds which are composed of sodium oxide and silicon dioxide and which may occur in various molar ratios (monosilicate, metasilicate and polysilicate). One example of a sodium silicate is the sodium salt of orthosilicic acid having the empirical formula $Na_4SiO_4$, which is also known as sodium orthosilicate.

Other examples of suitable sodium silicates are disodium metasilicate or sodium metasilicate having the empirical formula $Na_2SiO_3$, disodium disilicate having the empirical formula $Na_2Si_2O_5$, or disodium trisilicate having the empirical formula $Na_2Si_3O_7$.

Silicates in amorphous form can be produced by melting together silicon dioxide and alkali metal oxide in molar ratios of between 1:1 and 4:1. The solids thus obtained are dissolved at approximately 150° C. and 5 bar vapor pressure in order to obtain a solution of the sodium silicates in water; these corresponding solutions are alkali water glasses.

"Alkali water glasses" refer to glass-like (amorphous) sodium silicates solidified from a melt, or to aqueous solutions thereof. The term "sodium water glass" is also used. Sodium water glasses are encompassed by the definition of the sodium silicates within this invention.

The molar composition of water glasses is usually 2 to 4 mol $SiO_2$ to 1 mol alkali metal oxide ($Na_2O$).

One example of a preferred sodium silicate is sodium water glass which is in the form of its aqueous solution, has an $Na_2O$ content of 7.5 to 8.8% by weight and an $SiO_2$ content of 25.0 to 28.5% by weight, and which has the CAS No. 1344-09-5 (Chemical Abstracts Number).

Other coloring or bleaching agents which are preferred according to the invention includes at least one sodium silicate in a total amount of 0.1 to 9% by weight, preferably 0.2 to 8% by weight, particularly preferably 1 to 7.5% by weight, in each case based on the total weight of the coloring or bleaching agent according to the invention.

Other alkalizing agents, such as potassium hydroxide (KOH) and sodium hydroxide (NaOH), may also be included therein, usually in a total amount of 0.05 to 1.5% by weight, preferably 0.1 to 0.6% by weight, in each case based on the total weight of the coloring or bleaching agent according to the invention.

It has also surprisingly been found that the reduced hair-damaging effect of the coloring or bleaching agents according to the invention and preferred according to the invention can be further supported if at least one compound of general formula (III) is included therein.

Coloring or bleaching agents which are preferred according to the invention therefore include (a) at least one compound of general formula (III)

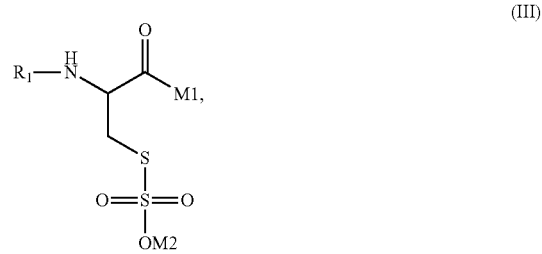

(III)

wherein

R1 represents a hydrogen atom or a structural element of formula (IV)

(IV)

, wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

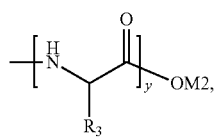

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$.

The essential ingredient (a) of formula (III) is the Bunte salt of an amino acid, oligopeptide or peptide, which is a compound of formula (III)

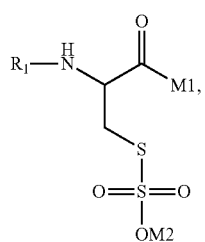

wherein
R1 represents a hydrogen atom or a structural element of formula (IV)

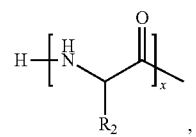

wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

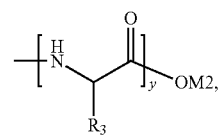

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$.

The radical R1 may represent either a hydrogen atom or a structural element of formula (IV)

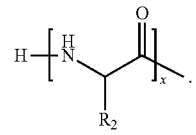

The structural element of formula (IV) is also characterized by the repeat index x, where x represents an integer from 1 to 100. The repeat index x indicates how many structural elements of formula (IV) are included in the compound of formula (III).

Preferably, x represents an integer from 1 to 50. More preferably, x represents an integer from 1 to 20. With very particular preference, x represents an integer from 1 to 10.

If x represents for example the number 10, the compound of formula (III) includes 10 structural elements of formula (IV).

It is essential here that the radical R2 in each of the structural elements of formula (IV) can in each case be selected independently of the preceding structural element of formula (IV). If, for example, the compounds of formula (III) includes 10 structural units of formula (IV), then these 10 structural units may be identical or different.

The radical R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group.

The structural element of formula (IV) is thus an amino acid which is peptide-linked via its amino and/or acid function within the compound of formula (III). If the amino acid is cysteine, this may also be in the form of a Bunte salt.

If the radical R2 represents a hydrogen atom, then the structural element of formula (IV) is based on the amino acid glycine.

If the radical R2 represents a methyl group, then the structural element of formula (IV) is based on the amino acid alanine.

If the radical R2 represents an isopropyl group (that is to say a group $(H_3C)_2CH—$), then the structural element of formula (IV) is based on the amino acid valine.

If the radical R2 represents a 2-methylpropyl group (that is to say a group $(H_3C)_2CH—CH_2—$), then the structural element of formula (IV) is based on the amino acid leucine.

If the radical R2 represents a 1-methylpropyl group (that is to say a group H3C—CH2-CH(CH3)-), then the structural element of formula (IV) is based on the amino acid isoleucine.

If the radical R2 represents a benzyl group (that is to say a group $C_6H_5—CH_2—$), then the structural element of formula (IV) is based on the amino acid phenylalanine.

If the radical R2 represents a 4-hydroxybenzyl group (that is to say a group 4-OH—$C_6H_5—CH_2—$), then the structural element of formula (IV) is based on the amino acid tyrosine.

If the radical R2 represents a hydroxymethyl group (that is to say a group HO—CH2-), then the structural element of formula (IV) is based on the amino acid serine.

If the radical R2 represents a 1-hydroxyethyl group (that is to say a group H3C—CH(OH)—), then the structural element of formula (IV) is based on the amino acid threonine.

If the radical R2 represents a 4-aminobutyl group (that is to say a group H2N—CH2-CH2-CH2-CH2-), then the structural element of formula (IV) is based on the amino acid lysine.

If the radical R2 represents a 3-carbamimidamidopropyl group (that is to say a group $H_2N—C(NH)—NH—CH_2—CH_2—CH_2—$), then the structural element of formula (IV) is based on the amino acid arginine.

If the radical R2 represents a 2-carboxyethyl group (that is to say a group HOOC—CH2-CH2-), then the structural element of formula (IV) is based on the amino acid glutamic acid.

If the radical R2 represents a carboxymethyl group (that is to say a group HOOC—CH2-), then the structural element of formula (IV) is based on the amino acid aspartic acid.

If the radical R2 represents a 2-carbamoylethyl group (that is to say a group H2N—C(O)—CH2-CH2-), then the structural element of formula (IV) is based on the amino acid glutamine.

If the radical R2 represents a carbamoylmethyl group (that is to say a group H2N—C(O)—CH2-), then the structural element of formula (IV) is based on the amino acid asparagine.

If the radical R2 represents a sulfanylmethyl group (that is to say a group HS—CH2-), then the structural element of formula (IV) is based on the amino acid cysteine.

If the radical R2 represents a 2-(methylsulfanyl)ethyl group (that is to say a group H3C—S—CH2-CH2-), then the structural element of formula (IV) is based on the amino acid methionine.

If the radical R2 represents a 1H-imidazol-4-ylmethyl group, then the structural element of formula (IV) is based on the amino acid histidine.

If the radical R2 represents a 1H-indol-3-ylmethyl group, then the structural element of formula (IV) is based on the amino acid tryptophan.

Finally, the radical R2 may also represent a (sulfosulfanyl)methyl group; in this case, it is a Bunte salt structure of formula $HO—S(O_2)—S—CH_2—$.

Depending on the pH of the coloring or bleaching agent, the Bunte salt structure of formula $HO—S(O_2)—S—CH_2—$ may also be in its deprotonated form.

Within the compound of formula (III), M1 represents the group —OM2 or a structural element of formula (V)

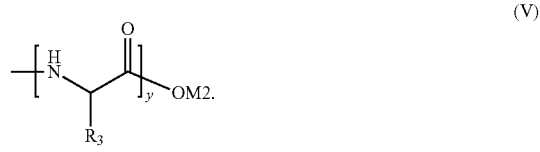

(V)

The structural element of formula (V) is characterized by the repeat index y, where y represents an integer from 1 to 100. The repeat index y indicates how many structural elements of formula (V) are included in the compound of formula (III).

Preferably, y represents an integer from 1 to 50. More preferably, y represents an integer from 1 to 20. With very particular preference, y represents an integer from 1 to 10.

If y represents for example the number 10, the compound of formula (III) includes 10 structural elements of formula (V).

It is essential here that the radical R3 in each of the structural elements of formula (V) can in each case be selected independently of the preceding structural element of formula (V). If, for example, the compounds of formula (III) includes 10 structural units of formula (V), then these 10 structural units may be identical or different.

The radical R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group.

The structural element of formula (V) is thus also an amino acid which is peptide-linked via its amino and/or acid function within the compound of formula (III). If the amino acid is cysteine, this may also be in the form of a Bunte salt.

If the radical R3 represents a hydrogen atom, then the structural element of formula (V) is based on the amino acid glycine.

If the radical R3 represents a methyl group, then the structural element of formula (V) is based on the amino acid alanine.

If the radical R3 represents an isopropyl group (that is to say a group $(H_3C)_2CH—$), then the structural element of formula (V) is based on the amino acid valine.

If the radical R3 represents a 2-methylpropyl group (that is to say a group $(H_3C)_2CH—CH_2—$), then the structural element of formula (V) is based on the amino acid leucine.

If the radical R3 represents a 1-methylpropyl group (that is to say a group H3C—CH2-CH(CH3)-), then the structural element of formula (V) is based on the amino acid isoleucine.

If the radical R3 represents a benzyl group (that is to say a group $C_6H_5—CH_2—$), then the structural element of formula (V) is based on the amino acid phenylalanine.

If the radical R3 represents a 4-hydroxybenzyl group (that is to say a group $4OH—C_6H_5—CH_2—$), then the structural element of formula (V) is based on the amino acid tyrosine.

If the radical R3 represents a hydroxymethyl group (that is to say a group HO—CH2-), then the structural element of formula (V) is based on the amino acid serine.

If the radical R3 represents a 1-hydroxyethyl group (that is to say a group H3C—CH(OH)—), then the structural element of formula (V) is based on the amino acid threonine.

If the radical R3 represents a 4-aminobutyl group (that is to say a group H2N—CH2-CH2-CH2-CH2-), then the structural element of formula (V) is based on the amino acid lysine.

If the radical R3 represents a 3-carbamimidamidopropyl group (that is to say a group $H_2N—C(NH)—NH—CH_2—CH_2—CH_2—$), then the structural element of formula (V) is based on the amino acid arginine.

If the radical R3 represents a 2-carboxyethyl group (that is to say a group HOOC—CH2-CH2-), then the structural element of formula (V) is based on the amino acid glutamic acid.

If the radical R3 represents a carboxymethyl group (that is to say a group HOOC—CH2-), then the structural element of formula (V) is based on the amino acid aspartic acid.

If the radical R3 represents a 2-carbamoylethyl group (that is to say a group $H_2N—C(O)—CH_2$-CH2-), then the structural element of formula (V) is based on the amino acid glutamine.

If the radical R3 represents a carbamoylmethyl group (that is to say a group H2N—C(O)—CH2-), then the structural element of formula (V) is based on the amino acid asparagine.

If the radical R3 represents a sulfanylmethyl group (that is to say a group HS—CH2-), then the structural element of formula (V) is based on the amino acid cysteine.

If the radical R3 represents a 2-(methylsulfanyl)ethyl group (that is to say a group H3C—S—CH2-CH2-), then the structural element of formula (V) is based on the amino acid methionine.

If the radical R3 represents a 1H-imidazol-4-ylmethyl group, then the structural element of formula (V) is based on the amino acid histidine.

If the radical R3 represents a 1H-indol-3-ylmethyl group, then the structural element of formula (V) is based on the amino acid tryptophan.

Finally, the radical R3 may also represent a (sulfosulfanyl)methyl group. This is a Bunte salt structure of formula $HO—S(O_2)—S—CH_2—$.

Here, too, depending on the pH of the coloring or bleaching agent, the Bunte salt structure of formula $HO—S(O_2)—S—CH_2—$ may also be in its deprotonated form.

The radical M2 represents a hydrogen atom, an equivalent of a monovalent or polyvalent cation or an ammonium ion $(NH_4)^+$.

As preferred equivalents of a monovalent or polyvalent cation, mention may be made in particular of the cations of sodium and potassium ($Na^+$ and $K^+$) or also magnesium or calcium (½ $Mg^{2+}$ or ½ $Ca^{2+}$).

If M2 represents a hydrogen atom, then the group —OM2 is the group —OH. If M2 represents a sodium cation, then the group —OM2 is the group —ONa. If M2 represents a potassium cation, then the group —OM2 is the group —OK. If M2 represents an ammonium ion, then the group —OM2 is the group $—O(NH_4)$.

The group —OM2 is always adjacent to a carbonyl group. To sum up, when M2 represents H, K, Na or ammonium, it therefore exists in the compound of formula (III) either in the form of an acid in its protonated form or else the sodium, potassium or ammonium salt of said acid.

The compounds of formula (III) according to the invention are either the Bunte salt of the amino acid cysteine, the Bunte salts of oligopeptides, or the Bunte salts of peptides.

If the radical R1 represents a hydrogen atom and the radical M1 represents a group —OM2, then the compound of formula (III) is the Bunte salt of the amino acid cysteine. In this case, the compound of formula (III) is the compound of formula (IIIa),

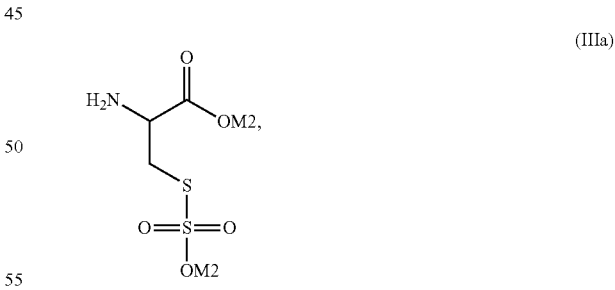

(IIIa)

wherein M2 is again defined as described above.

If the compound of formula (IIIa) is in the form of its free acid, it is 2-amino-3-(sulfosulfanyl)propanoic acid. This substance is commercially available.

It has been found that the use of the compound of formula (IIIa) in coloring or bleaching agents, even in particularly small use amounts, leads to a particularly effective reduction in damage to the hair, said reduction still persisting even after repeated washing of the hair. The use of compounds of formula (IIIa) in coloring or bleaching agents is therefore very particularly preferred.

In one very particularly preferred embodiment, a coloring or bleaching agent according to the invention is characterized in that it includes at least one compound of formula (III), wherein
R1 represents a hydrogen atom and
M1 represents a group —OM2.

If a compound of formula (IIIa) is used, preferably said specific compound is used. If, however, the Bunte salts of oligopeptides are used as compounds of formula (III), then the coloring or bleaching agent according to the invention may also includes multiple compounds of formula (III) as a mixture of different oligopeptides. These oligopeptides are defined by their average molecular weight. The average molecular weight $M_w$ of the at least one oligopeptide of formula (III) can be determined for example by gel permeation chromatography (GPC) using polystyrene as the internal standard according to DIN 55672-3, Version 8/2007.

Depending on how many structural elements of formula (IV) and/or (V) are included in the compound of formula (III), and depending on the type of said amino acids, the molecular weight of the compound of formula (III) used according to the invention may vary. It is particularly preferred according to the invention if the compound of formula (III) is an oligopeptide which has a molecular weight $M_w$ of 200 to 2000 Da, preferably 250 to 1500 Da, preferably 300 to 1200 Da, in particular 400 to 800 Da.

In the context of the present invention, the term "oligopeptide" will be understood to mean condensation products of amino acids which have the molecular weights specified above.

In one very particularly preferred embodiment, a coloring or bleaching agent according to the invention is characterized in that it includes at least one compound of formula (III) which has a molecular weight $M_w$ of 200 to 2000 Da (Dalton), preferably 250 to 1500 Da, more preferably 300 to 1200 Da, in particular 400 to 800 Da.

If a mixture of oligomers is used in the coloring or bleaching agent according to the invention, these mixtures can be defined by their average molecular weight.

In this case, a preferred coloring or bleaching agent according to the invention is characterized in that it includes at least one mixture of compounds of formula (III) which has an average molecular weight $M_w$ of 200 to 2000 Da, preferably 250 to 1500 Da, more preferably 300 to 1200 Da, in particular 400 to 800 Da.

It has also been found that the protective effect or repair effect exhibited by the compounds of formula (III) also depends on the repeat indices x and y. As described above, it is very particularly preferred if x represents an integer from 1 to 10 and y represents an integer from 1 to 10.

In another very particularly preferred embodiment, a coloring or bleaching agent according to the invention is characterized in that it includes at least one compound of formula (III), wherein
R1 represents a structural element of formula (IV), and
M1 represents a structural element of formula (V), and
x represents an integer from 1 to 10 and
y represents an integer from 1 to 10.

Besides the molecular weight of the compound of formula (III), the amount of Bunte salt units included in the compound of formula (III) also has a critical influence on the efficacy of the protective effect or "repair effect" of the compounds.

Compounds having at least one Bunte salt unit—as is present for example in the compound of formula (IIIa)—are very effective, particularly when they are used as a monomeric compound. Oligopeptides having at least one Bunte salt unit are particularly effective when they have a low molecular weight of up to 1200, in particular 800 Dalton.

When using oligopeptides, however, it is of very particular advantage if the compound of formula (III) has at least two, preferably at least three Bunte salt units.

In another very particularly preferred embodiment, a coloring or bleaching agent according to the invention is characterized in that it includes at least one compound of formula (III), wherein
R1 represents a structural element of formula (IV), and
the radical R2 in at least one structural element of formula (IV) represents a (sulfosulfanyl)-methyl group (that is to say a group HO—S($O_2$)—S—$CH_2$—).

In another very particularly preferred embodiment, a coloring or bleaching agent according to the invention is characterized in that it includes at least one compound of formula (III), wherein
R1 represents a structural element of formula (IV), and
x represents an integer of at least 3 and
the radical R2 in at least 3 structural elements of formula (IV) represents a 2-carboxyethyl group (that is to say a group HOOC—CH2-CH2-).

In another very particularly preferred embodiment, a coloring or bleaching agent according to the invention is characterized in that it includes at least one compound of formula (III), wherein
M1 represents a structural element of formula (V), and
y represents an integer of at least 3 and
the radical R3 in at least 3 structural elements of formula (IV) represents a group (Glu).

The at least one compound of formula (III) is included in a total amount of 0.001 to 10% by weight, based on the total weight of the coloring or bleaching agent preferred according to the invention. However, it has surprisingly been found that the compound(s) of formula (III) can bring about a very good reduction in damage to the hair even when used in low concentrations. This is particularly advantageous when the at least one compound of formula (III) is to be added to the coloring or bleaching agent according to the invention as an additive (for example in the form of a care solution or repair solution) prior to application to the hair. For this reason, it is particularly advantageous if the coloring or bleaching agent preferred according to the invention includes one or more compounds of the above formula (III) in a total amount of 0.001 to 2.5% by weight, more preferably 0.01 to 1.0% by weight and particularly preferably 0.02 to 0.1% by weight, in each case based on the weight of the coloring or bleaching agent according to the invention.

In another very particularly preferred embodiment, a coloring or bleaching agent according to the invention is characterized in that it includes one or more compounds of the above formula (III) in a total amount of 0.001 to 2.5% by weight, more preferably 0.01 to 1.0% by weight and particularly preferably 0.02 to 0.1% by weight, in each case based on the weight of the coloring or bleaching agent according to the invention.

Water

The coloring or bleaching agents according to the invention includes water, namely preferably in an amount of 20 to 85% by weight, preferably 30 to 80% by weight, in each case based on the total weight of the coloring or bleaching agent according to the invention.

Peroxide Compounds

The development of the dyes in oxidative coloring agents or the breakdown of the hair's own pigment melanin for bleaching purposes takes place by the effect of a peroxide compound as an oxidizing agent. Usually, hydrogen peroxide is used for this. Hydrogen peroxide can only be used in the form of an aqueous solution.

Coloring or bleaching agents which are preferred according to the invention are characterized in that they includes 0.5 to 13% by weight, more preferably 1 to 7% by weight, particularly preferably 2 to 6% by weight and very particularly preferably 3 to 4.5% by weight hydrogen peroxide (calculated as 100% strength $H_2O_2$), in each case based on the total weight of the coloring or bleaching agent according to the invention.

Bleaching agents or coloring agents with a particularly strong lightening effect may moreover includes strongly oxidizing peroxide compounds, such as potassium, sodium and/or ammonium persulfate.

It has proven to be advantageous if the oxidizing agent preparations according to the invention additionally includes at least one stabilizer or complexing agent for stabilizing the hydrogen peroxide. Particularly preferred stabilizers are in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP), or sodium salts thereof.

If the agents according to the invention are agents for the oxidative coloring of keratin fibers, in particular human hair, these includes at least one oxidation dye precursor for developing the dyes.

Oxidation dye precursors includes oxidation dye precursors of the developer type and of the coupler type. Particularly suitable oxidation dye precursors of the developer type are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof.

Particularly suitable oxidation dye precursors of the coupler type are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

In one preferred embodiment, the coloring agents according to the invention includes one or more oxidation dye precursors in a total amount of 0.01 to 4.0% by weight, preferably 0.1 to 3.5% by weight, more preferably 0.6 to 3.1% by weight and very particularly preferably 1.2 to 2.2% by weight, based on the total weight of the coloring or bleaching agent according to the invention.

In another preferred embodiment, the agents according to the invention additionally includes at least one further substantive dye. Substantive dyes can be subdivided into anionic, cationic and nonionic substantive dyes. The substantive dyes are preferably selected from nitrophenylenediamines, nitroaminophenols, azo dyes, anthraquinones, triarylmethane dyes or indophenols, and the physiologically acceptable salts thereof. The substantive dyes are in each case used preferably in a total amount of 0.001 to 2% by weight, based on the total weight of the coloring or bleaching agent according to the invention. Substantive dyes are used in oxidative coloring agents for nuancing the shade achieved, and in oxidative bleaching agents for balancing out undesired red tones which may be produced as the melanin in the hair breaks down.

Preferred anionic substantive dyes are the compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

Preferred cationic substantive dyes are cationic triphenylmethane dyes, such as for example Basic Blue 7, Basic Blue 26, Basic Violet 2 and Basic Violet 14, aromatic systems substituted with a quaternary nitrogen group, such as for example Basic Yellow 57, Basic Red 76, Basic Blue 99, Basic Brown 16 and Basic Brown 17, cationic anthraquinone dyes, such as HC Blue 16 (Bluequat B), and substantive dyes which includes a heterocycle having at least one quaternary nitrogen atom, in particular Basic Yellow 87, Basic Orange 31 and Basic Red 51. The cationic substantive dyes marketed under the trade name Arianor are cationic substantive dyes which are also preferred according to the invention.

Nonionic nitro and quinone dyes and neutral azo dyes are particularly suitable as nonionic substantive dyes. Preferred nonionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3- nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Optional: Polymer A Having at Least 10 Constituent Units of Formula (I)

Oxidative coloring or bleaching agents which are preferred according to the invention optionally includes at least one polymer A which has at least ten constituent units of formula (I)

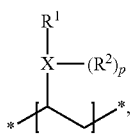
(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units.

It has surprisingly been found that a polymer A as described above and as will be explained in more detail below superbly supports the protective effect and repair effect exerted by the combination of at least one saturated dicarboxylic acid having 2 to 10 carbon atoms and/or at least one salt of said acid(s) and at least one amino acid of formula (VI), as explained above, on oxidatively colored or bleached keratin fibers.

In the context of the present invention, "polymer" will be understood to mean polymers as per the IUPAC definition, which include at least 10 identical constituent units.

According to RÖMPP Chemie Lexikon, as at July 2009, according to the IUPAC definition the term "polymer" refers to a substance which is composed of a collective of macromolecules (polymer molecules) constructed from chemical units, said macromolecules or polymer molecules differing from one another by the degree of polymerization, molecular weight and chain length. In such substances formed of so-called polymer units, therefore, all macromolecules are of identical construction and differ only in their chain length (degree of polymerization). According to this IUPAC definition, a polymer is also "a polyreaction product which is constructed from a plurality of molecules in which one type or a plurality of types of atoms or atom groups (so-called constituent units, basic building blocks or repeat units) are repeatedly lined up next to one another.

The number of constituent units in a polymer is referred to as the degree of polymerization. Polymers A and polymers B which are preferred according to the invention have in each case a degree of polymerization in the range from 40 to 1000, preferably 100 to 800, particularly preferably 350 to 650. Other polymers A having at least ten constituent units of formula (I) which are preferred according to the invention includes 40 to 1000, preferably 100 to 800, particularly preferably 350 to 650 identical constituent units of formula (I).

$R^1$ and $R^2$ preferably each independently of one another represent hydrogen or a $C_2$-$C_{10}$ acyl group which is preferably selected from an acetyl, propanoyl or n-butanoyl group, particularly preferably selected from an acetyl group.

Polymers A which are preferred according to the invention have at least 10 constituent units of formula (I), in which X represents nitrogen, the polymer A including no permanently ionic constituent units.

Other polymers A which are particularly preferred according to the invention have at least 10 constituent units of formula (I), in which X represents nitrogen and $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group.

If $R^1$ and $R^2$ together with X form a five-membered or six-membered, saturated or unsaturated ring which optionally includes further heteroatoms preferably selected from N and O, said ring is preferably substituted with at least one functional group selected from =O. One particularly preferred substituent combination X, $R^1$, $R^2$ is a pyrrolidone group, so that a constituent unit of formula (I) which is particularly preferred according to the invention is a unit of formula (Ia)

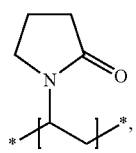
(Ia)

in which X represents nitrogen and $R^1$ and $R^2$ together with said nitrogen atom form a five-membered, saturated ring which includes no further heteroatoms and which is substituted in the 2-position with a functional group =O.

Another particularly preferred substituent combination X, $R^1$, $R^2$ is an ε-caprolactam group, so that a constituent unit of formula (I) which is particularly preferred according to the invention is a unit of formula (I b)

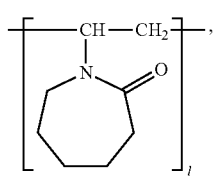
(Ib)

in which X represents nitrogen and $R^1$ and $R^2$ together with said nitrogen atom form a six-membered, saturated ring which includes no further heteroatoms and which is substituted with a functional group =O.

Another particularly preferred substituent combination X, $R^1$, $R^2$ is an imidazole group, so that another unit of formula (I) which is particularly preferred according to the invention is a unit in which X represents nitrogen and $R^1$ and $R^2$ together with said nitrogen atom form a five-membered, unsaturated ring which includes nitrogen as a further heteroatom.

Other polymers A which are preferred according to the invention include 25-100 mol %, preferably 55-100 mol %, particularly preferably 85-100 mol % constituent units of formula (I) in which X represents nitrogen, the polymer A including no permanently ionic constituent units.

Other polymers A which are preferred according to the invention include 25-100 mol %, preferably 55-100 mol %, particularly preferably 85-100 mol % constituent units of formula (I) in which X represents nitrogen and $R^1$ and $R^2$ together with X form a five-membered or six-membered, saturated or unsaturated ring which optionally includes further heteroatoms selected from N and O and is optionally substituted with at least one C1-C6 alkyl group and/or with at least one functional group, the polymer A including no permanently ionic constituent units.

Polymers A which are particularly preferred according to the invention include 98-100 mol % constituent units of formula (Ia), the polymer A including no permanently ionic constituent units.

Polymers A which are extremely preferred according to the invention include 98-100 mol % constituent units of formula (Ia) and have a degree of polymerization in the range from 40 to 1000, preferably 100 to 800, particularly preferably 350 to 650, the polymer A including no permanently ionic constituent units Particularly preferred polymers A are polyvinylpyrrolidone homopolymers having a degree of polymerization in the range from 40 to 1000, preferably 100 to 800, particularly preferably 350 to 650.

Another particularly preferred substituent combination X, $R^1$, $R^2$ is a constituent unit of formula (I) in which X represents oxygen, p is zero and $R^1$ represents hydrogen.

Another particularly preferred substituent combination X, $R^1$, $R^2$ is a constituent unit of formula (I) in which X represents oxygen, p is zero and $R^1$ represents an acetyl group.

Other polymers A which are preferred according to the invention includes 75-92 mol % constituent units of formula (I) in which X represents oxygen, p is zero and $R^1$ represents hydrogen, and 8-25 mol % constituent units of formula (I) in which X represents oxygen, p is zero and $R^1$ represents an acetyl group, the polymer A including no permanently ionic constituent units.

Other polymers A which are preferred according to the invention includes 40 to 1000, preferably 100 to 800, particularly preferably 350 to 650 constituent units of formula (I), of which 75-92 mol % constituent units of formula (I) in which X represents oxygen, p is zero and $R^1$ represents hydrogen, and 8-25 mol % constituent units of formula (I) in which X represents oxygen, p is zero and $R^1$ represents an acetyl group, the polymer A including no permanently ionic constituent units.

Other polymers A which are preferred according to the invention includes 65-25 mol % constituent units of formula (Ia) and 35-75 mol % constituent units of formula (I) in which X represents oxygen, p is zero and $R^1$ represents an acetyl group, the polymer A including no permanently ionic constituent units.

Other polymers A which are preferred according to the invention includes 40 to 1000, preferably 100 to 800, particularly preferably 350 to 650 constituent units of formula (I), of which 65-25 mol % constituent units of formula (Ia) and 35-75 mol % constituent units of formula (I) in which X represents oxygen, p is zero and $R^1$ represents an acetyl group, the polymer A including no permanently ionic constituent units.

The at least one polymer A having at least ten constituent units of formula (I) has no permanently ionic charges. However, it is possible that the constituent units of formula (I) are in ionic form, in particular in cationic form, for example due to protonation of the nitrogen atom in an acidic carrier. However, these charges are not permanent but rather are temporary since they depend on the surrounding medium.

Preferred coloring or bleaching agents according to the invention includes the at least one polymer A having at least ten constituent units of formula (I) in a total amount of 0.2 to 5% by weight, preferably 0.5 to 3% by weight, particularly preferably 1.0 to 2.3% by weight, in each case based on the weight of the coloring or bleaching agent.

As a further optional ingredient, coloring or bleaching agents which are preferred according to the invention includes at least one permanently cationic polymer B.

Besides at least one permanently cationically charged monomer type, the permanently cationic polymer preferably also includes at least one permanently anionically charged monomer type, the cationic monomers being present in molar excess relative to the anionic monomers so that the at least one second polymer according to the invention has a cationic net charge. Such polymers which are preferred according to the invention are also referred to as amphoteric or zwitterionic polymers.

In another preferred embodiment, coloring or bleaching agents which are preferred according to the invention includes at least one permanently cationic polymer selected from cationic polymers constructed from monomers with quaternary ammonium groups of general formula (IIa),

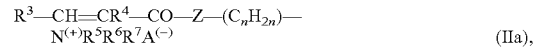

(IIa), in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, preferably selected from cationic polymers constructed from acrylamidopropyl trimethylammonium chloride, particularly preferably selected from amphoteric polymers having a cationic net charge which are constructed by polymerization from a) cationic monomers with quaternary ammonium groups of general formula (IIa),

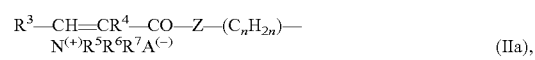

(IIa), in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, and b) at least one unsaturated carboxylic acid selected from acrylic acid, methacrylic acid and crotonic acid and from mixtures of said acids, wherein the at least one unsaturated carboxylic acid may be in the form of its salts, wherein in the polymer the cationic monomers are in molar excess relative to the anionic monomers;
extremely preferably selected from amphoteric polymers having a cationic net charge which includes the at least one monomer type of general formula (IIa) and the at least one monomer type of the unsaturated carboxylic acid, selected from acrylic acid, methacrylic acid and crotonic acid and mixtures thereof, in a molar ratio of 60:40 to 95:5, preferably 75:25 to 90:10,
most extremely preferably selected from amphoteric copolymers having a cationic net charge which consist of acrylamidopropyl trimethylammonium chloride and acrylic acid in a molar ratio of 60:40 to 95:5, preferably 75:25 to 90:10;
2-[2-hydroxy-3-(trimethylammonio)propoxy]ethyl cellulose ether chloride, which is obtainable for example under the INCI name Polyquaternium-10,
terpolymers of acrylic acid, diallyldimethylammonium chloride and acrylamide, such as those obtainable for example under the INCI name Polyquaternium-39,
homopolymers of N,N,N-trimethyl-2-[(methyl-1-oxo-2-propenyl)oxy]ethanaminium chloride, such as those obtainable for example under the INCI name Polyquaternium-37,
copolymers of diallyldimethylammonium chloride and acrylic acid, such as those obtainable for example under the INCI name Polyquaternium-22,
hydroxyethyl cellulose/dimethyldiallylammonium chloride copolymers, such as those obtainable for example under the INCI name Polyquaternium-4,
copolymers of acrylamide and beta-methacryloxyethyltrimethyl ammonium methosulfate, such as those obtainable for example under the INCI name Polyquaternium-5,
homopolymers of N,N-dimethyl-N-2-propenyl-2-propen-1-aminium chloride, such as those obtainable for example under the INCI name Polyquaternium-6,
copolymers of diallyldimethylammonium chloride and acrylamide, such as those obtainable for example under the INCI name Polyquaternium-7,
copolymers of vinylpyrrolidone and dimethylaminoethyl methacrylate diethyl sulfate, such as those obtainable for example under the INCI name Polyquaternium-11,
and mixtures of the aforementioned polymers.

Permanent cationic polymers which are extremely preferred according to the invention are selected from 2-[2-hydroxy-3-(trimethylammonio)propoxy]ethyl cellulose ether chloride, amphoteric copolymers having a cationic net charge which consist of acrylamidopropyl trimethylammonium chloride and acrylic acid in a molar ratio of 60:40 to 95:5, preferably 75:25 to 90:10, and terpolymers of acrylic acid, diallyldimethylammonium chloride and acrylamide, as well as mixtures of two or three of said polymers.

Particularly preferred polymer B mixtures includes 2-[2-hydroxy-3-(trimethylammonio)-propoxy]ethyl cellulose ether chloride and at least one amphoteric copolymer having a cationic net charge which consists of acrylamidopropyl trimethylammonium chloride and acrylic acid in a molar ratio of 60:40 to 95:5, preferably 75:25 to 90:10.

Other particularly preferred polymer B mixtures includes 2-[2-hydroxy-3-(trimethylammonio)propoxy]ethyl cellulose ether chloride, at least one amphoteric copolymer having a cationic net charge which consists of acrylamidopropyl trimethylammonium chloride and acrylic acid in a molar ratio of 60:40 to 95:5, preferably 75:25 to 90:10, and at least one terpolymer of acrylic acid, diallyldimethylammonium chloride and acrylamide.

Permanently cationic polymers B which are likewise extremely preferred according to the invention are selected from Polyquaternium-10, amphoteric copolymers having a cationic net charge which consist of acrylamidopropyl trimethylammonium chloride and acrylic acid in a molar ratio of 60:40 to 95:5, preferably 75:25 to 90:10, and Polyquaternium-39, as well as mixtures of two or three of said polymers.

Other particularly preferred polymer B mixtures includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10.

Other particularly preferred polymer B mixtures includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, and Polyquaternium-39.

Preferred coloring or bleaching agents according to the invention includes the at least one permanently cationic polymer B in a total amount of 0.05 to 1.5% by weight, preferably 0.1 to 1.0% by weight, particularly preferably 0.2 to 0.8% by weight, in each case based on the weight of the coloring or bleaching agent according to the invention.

Other particularly preferred coloring or bleaching agents includes 2-[2-hydroxy-3-(trimethylammonio)-propoxy]ethyl cellulose ether chloride and at least one amphoteric copolymer having a cationic net charge which consists of acrylamidopropyl trimethylammonium chloride and acrylic acid in a molar ratio of 60:40 to 95:5, preferably 75:25 to 90:10, in a total amount of 0.05 to 1.5% by weight, preferably 0.1 to 1.0% by weight, particularly preferably 0.2 to 0.8% by weight, in each case based on the weight of the coloring or bleaching agent according to the invention.

Other particularly preferred coloring or bleaching agents includes 2-[2-hydroxy-3-(trimethylammonio)propoxy]ethyl cellulose ether chloride, at least one amphoteric copolymer having a cationic net charge which consists of acrylamidopropyl trimethylammonium chloride and acrylic acid in a molar ratio of 60:40 to 95:5, preferably 75:25 to 90:10, and at least one terpolymer of acrylic acid, diallyldimethylammonium chloride and acrylamide, in a total amount of 0.05 to 1.5% by weight, preferably 0.1 to 1.0% by weight, particularly preferably 0.2 to 0.8% by weight, in each case based on the weight of the coloring or bleaching agent according to the invention.

Other particularly preferred coloring or bleaching agents includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, in a total amount of 0.05 to 1.5% by weight, preferably 0.1 to 1.0% by weight, particularly preferably 0.2 to 0.8% by weight, in each case based on the weight of the coloring or bleaching agent according to the invention.

Other particularly preferred coloring or bleaching agents includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, and Polyquaternium-39, in a total amount of 0.05 to 1.5% by weight, preferably 0.1 to 1.0% by weight, particularly preferably 0.2 to 0.8% by weight, in each case based on the weight of the coloring or bleaching agent according to the invention.

Optional Amino Acids

The coloring or bleaching agents according to the invention may optionally includes at least one further amino acid which is different than the amino acids of formula (VI). Optional amino acids which are preferred according to the invention are selected from serine, alanine, aspartic acid, glutamic acid, glycine, isoleucine, leucine, phenylalanine, proline, threonine, tyrosine and valine, as well as mixtures of said amino acids. The optional amino acids may also be present in salt form, wherein in this case preference is given to the same salts and/or counter-ions as for the saturated dicarboxylic acids mentioned above.

It has surprisingly been found that a content of at least one amino acid selected from serine, alanine, aspartic acid, glutamic acid, glycine, isoleucine, leucine, phenylalanine, proline, threonine, tyrosine and valine, as well as mixtures of said amino acids, can further reduce the particularly slight hair-damaging effect of the coloring or bleaching agents according to the invention.

A particularly good effect was noted particularly for serine. Extremely preferred coloring or bleaching agents according to the invention includes serine and at least one of the basic amino acids arginine, histidine or lysine, wherein particularly preferably serine and at least one of the basic amino acids arginine, histidine or lysine are included in a molar ratio of serine to total basic amino acids in the range of 1:1 to 50:1, preferably 5:1 to 30:1.

Other coloring or bleaching agents which are preferred according to the invention are characterized in that the at least one optional amino acid is included in a total amount of 0.5 to 5% by weight, preferably 0.7 to 3% by weight, particularly preferably 0.9 to 2% by weight, in each case based on the weight of the coloring or bleaching agent.

Another subject matter of the present invention is a method for the oxidative coloring and/or lightening of keratin fibers, in particular of human hair, in which a coloring or bleaching agent is applied to the keratin fibers, in particular to the human hair, and is rinsed out again after a leave-in time of 0.1 to 60 minutes, preferably 1 to 45 minutes, particularly preferably 10 to 30 minutes, said coloring or bleaching agent including a) at least one saturated dicarboxylic acid having 2 to 10 carbon atoms and/or at least one salt of said acid(s), b) at least one amino acid of formula (VI)

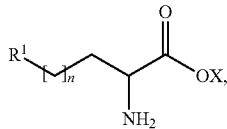

(VI)

in which

X represents a hydrogen atom or a monovalent or divalent cation;

n represents zero, 1, 2 or 3;

$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid, c) also at least one alkalizing agent, selected from ammonium hydroxide, monoethanolamine and sodium silicates, and mixtures thereof, d) optionally at least one oxidation dye precursor and/or at least one substantive dye, e) water, and f) at least one peroxide compound.

For the method according to the invention for the oxidative coloring and/or lightening of keratin fibers, in particular of human hair, and the preferred embodiments thereof, what has been stated above in relation to the coloring and bleaching agents according to the invention and preferred according to the invention applies, mutatis mutandis.

The method according to the invention for the oxidative coloring and/or lightening of keratin fibers, in particular of human hair, may optionally be followed by further hair treatment steps, for example the application of a conditioner, of a hair styling agent, for example a smoothing agent or waving agent, of a further hair coloring agent, for example for coloring or bleaching strands, rinsing steps and drying steps, for example rubbing or pressing dry with a towel, drying using a hairdryer, or drying using a drying hood.

It may be preferred according to the invention to store the hair-protecting combination according to the invention consisting of at least one saturated dicarboxylic acid having 2 to 10 carbon atoms and/or at least one salt of said acid(s) and at least one amino acid of formula (VI), as discussed above, initially separately from the preparation which includes the at least one alkalizing agent and optionally at least one oxidation dye precursor and/or at least one substantive dye, and separately from the oxidizing agent preparation which includes at least one peroxide compound, and to produce the coloring or bleaching agent according to the invention or preferred according to the invention by mixing the three components just before starting the method according to the invention or preferred according to the invention for the oxidative coloring and/or lightening of keratin fibers.

Another subject matter of the present invention is therefore a method for the oxidative coloring and/or lightening of keratin fibers, in particular of human hair, which includes the following method steps:

I. providing a composition (A), including a) at least one saturated dicarboxylic acid having 2 to 10 carbon atoms and/or at least one salt of said acid(s), b) at least one amino acid of formula (VI)

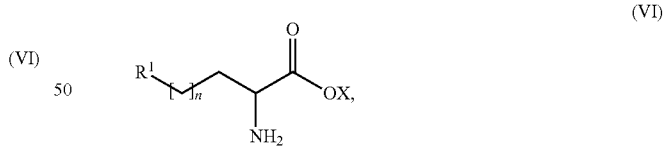

(VI)

in which

X represents a hydrogen atom or a monovalent or divalent cation;

n represents zero, 1, 2 or 3;

$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid, c) water, and d) optionally also at least one substance selected from compounds of general formula (III)

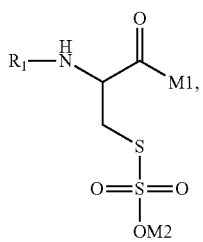

(III)

wherein

R1 represents a hydrogen atom or a structural element of formula (IV)

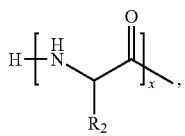

(IV)

wherein x represents an integer from 1 to 100, the radical R2 in each of the structural elements of formula (IV) can in each case be selected independently of the preceding structural element of formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 represents the group —OM2 or a structural element of formula (V)

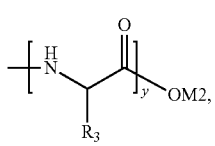

(V)

wherein y represents an integer from 1 to 100, the radical R3 in each of the structural elements of formula (V) can in each case be selected independently of the preceding structural element of formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 represents a hydrogen atom, an equivalent of a monovalent or polyvalent cation or an ammonium ion $(NH_4)^+$, and polymers A which have at least ten constituent units of formula (I)

(I)

in which

X represents nitrogen or oxygen and $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and p=0 when X represents oxygen and p=1 when X represents nitrogen, the polymer A including no permanently ionic constituent units, II. providing a composition (B), including
  e) at least one alkalizing agent, selected from ammonium hydroxide, monoethanolamine and sodium silicates, and mixtures thereof,
  f) optionally water, and
  g) optionally at least one oxidation dye precursor and/or at least one substantive dye, III. providing a composition (C), including
  h) at least one peroxide compound, which is preferably hydrogen peroxide, IV. mixing compositions (A), (B) and (C) with one another, then immediately V. applying the mixture of (A), (B) and (C) to the keratin fibers, in particular to the human hair, and VI. rinsing out after a leave-in time of 0.1 to 60 minutes, preferably 1 to 45 minutes, particularly preferably 10 to 30 minutes, VII. optionally further hair treatments, such as styling, conditioning and/or drying.

Mixing Ratios of Composition (A), Composition (B) and Composition (C)

It has proven to be effective according to the invention if the weight ratio of composition (A), which includes water and the hair-protecting combination consisting of at least one saturated dicarboxylic acid having 2 to 10 carbon atoms and at least one amino acid of formula (VI), the oxidatively coloring and/or oxidatively lightening mixture of composition (B), including at least one alkalizing agent and optionally oxidation dye precursors and/or substantive dyes, and composition (C), including at least one peroxide compound, is in the range of [weight of A]/[weight of B+weight of C] 1:4 to 1:50, preferably 1:5 to 1:25, particularly preferably 1:9 to 1:20, extremely preferably 1:10 to 1:15.

Coloring or lightening methods which are preferred according to the invention and which use the at least three aforementioned compositions (A), (B) and (C) are characterized in that the at least one saturated dicarboxylic acid having 2 to 10 carbon atoms is included in the composition (A) in a total amount of 2 to 20% by weight, preferably 5 to 15% by weight, particularly preferably 8 to 12% by weight, in each case converted to the undissociated dicarboxylic acid and based on the weight of the composition (A).

Coloring or lightening methods which are preferred according to the invention and which use the at least three aforementioned compositions (A), (B) and (C) are also characterized in that the at least one amino acid of formula (VI) and/or a salt thereof is included in the composition (A) in a total amount of 0.4 to 7.0% by weight, preferably 0.8 to 5.0% by weight, particularly preferably 1.5 to 4.0% by weight, in each case converted to the undissociated amino acid and based on the weight of the composition (A).

Coloring or lightening methods which are preferred according to the invention and which use the at least three aforementioned compositions (A), (B) and (C) are also characterized in that at least one polymer A which has at least ten constituent units of formula (I)

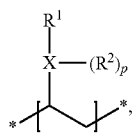

in which
X represents nitrogen or oxygen and
R$^1$ and R$^2$ in each case independently of one another represent hydrogen or a C2-C10 acyl group or R$^1$ and R$^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units,
is included in the composition (A) in a total amount of 0.5 to 14% by weight, preferably 1.0 to 11% by weight, particularly preferably 2.0 to 10% by weight, in each case based on the weight of the composition (A).

Other coloring or lightening methods which are preferred according to the invention and which use the at least three aforementioned compositions (A), (B) and (C) are characterized in that the composition (A) includes, in each case converted to the undissociated succinic acid, 2 to 20% by weight, preferably 5 to 15% by weight, particularly preferably 8 to 12% by weight succinic acid and at least one of the amino acids arginine, histidine or lysine and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A).

Other coloring or lightening methods which are preferred according to the invention and which use the at least three aforementioned compositions (A), (B) and (C) are characterized in that the composition (A) includes one or more compounds of the above formula (III) in a total amount of 0.001 to 1% by weight, more preferably 0.005 to 0.5% by weight and particularly preferably 0.01 to 0.1% by weight, in each case based on the weight of the composition (A).

Other coloring or lightening methods which are preferred according to the invention and which use the at least three aforementioned compositions (A), (B) and (C) are characterized in that the composition (A) includes 50 to 92% by weight, preferably 60 to 87% by weight and particularly preferably 65 to 80% by weight water, in each case based on the weight of the composition (A).

Other coloring or lightening methods which are preferred according to the invention and which use the at least three aforementioned compositions (A), (B) and (C) are characterized in that the composition (A) has a pH in the range from 3.5 to 7.1, preferably 4.5 to 6.5, particularly preferably 5.0 to 6.0, in each case measured at 20° C.

Other coloring or lightening methods which are preferred according to the invention and which use the at least three aforementioned compositions (A), (B) and (C) are characterized in that the composition (B) has a pH in the range from 6.5 to 11.0, preferably 8 to 10.5, particularly preferably 8.5 to 10.0, in each case measured at 20° C.

Other coloring or lightening methods which are preferred according to the invention and which use the at least three aforementioned compositions (A), (B) and (C) are characterized in that the composition (C) has a pH in the range from 2.5 to 6.5, preferably 3.0 to 5.5, particularly preferably 3.5 to 5.0, in each case measured at 20° C.

Other coloring or lightening methods which are preferred according to the invention and which use the at least three aforementioned compositions (A), (B) and (C) are characterized in that the composition (C) includes 1.0 to 23.0% by weight, more preferably 2.5 to 21.0% by weight, particularly preferably 4.0 to 20.0% by weight and very particularly preferably 5.0 to 18.0% by weight hydrogen peroxide (calculated as 100% strength $H_2O_2$), in each case based on the weight of the composition (C).

For the method according to the invention for the oxidative coloring and/or lightening of keratin fibers, in particular of human hair, using the at least three aforementioned compositions (A), (B) and (C), and the preferred embodiments thereof, what has been stated above in relation to the coloring and bleaching agents according to the invention and preferred according to the invention applies, mutatis mutandis, apart from the modified stated quantities mentioned above.

Another subject matter of the present invention is a composition (A) for treating hair, including
at least one saturated dicarboxylic acid having 2 to 10 carbon atoms in a total amount of 2 to 20% by weight, preferably 5 to 15% by weight, particularly preferably 8 to 12% by weight, in each case converted to the undissociated dicarboxylic acid and based on the weight of the composition (A), the dicarboxylic acid preferably being selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, also
at least one amino acid of formula (VI) and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), and
water, preferably in an amount of 50 to 92% by weight, particularly preferably 60 to 87% by weight and extremely preferably 65 to 80% by weight, in each case based on the weight of the composition (A).

Another subject matter of the present invention is a composition (A) for treating hair, including
- at least one saturated dicarboxylic acid having 2 to 10 carbon atoms in a total amount of 2 to 20% by weight, preferably 5 to 15% by weight, particularly preferably 8 to 12% by weight, in each case converted to the undissociated dicarboxylic acid and based on the weight of the composition (A), the dicarboxylic acid preferably being selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, also
- at least one of the amino acids arginine, histidine or lysine and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), and
- 50 to 92% by weight, particularly preferably 60 to 87% by weight and extremely preferably 65 to 80% by weight water, in each case based on the weight of the composition (A).

Another subject matter of the present invention is a composition (A) for treating hair, including
- at least one saturated dicarboxylic acid having 2 to 10 carbon atoms in a total amount of 2 to 20% by weight, preferably 5 to 15% by weight, particularly preferably 8 to 12% by weight, in each case converted to the undissociated dicarboxylic acid and based on the weight of the composition (A), the dicarboxylic acid preferably being selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, also
- at least one amino acid of formula (VI) and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), also
- water, preferably in an amount of 50 to 92% by weight, particularly preferably 60 to 87% by weight and extremely preferably 65 to 80% by weight, in each case based on the weight of the composition (A), and
- at least one polymer A which has at least ten constituent units of formula (I)

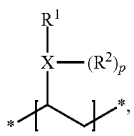

(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units,
in the composition (A) in a total amount of 0.5 to 14% by weight, preferably 1.0 to 11% by weight, particularly preferably 2.0 to 10% by weight, in each case based on the weight of the composition (A).

Another subject matter of the present invention is a composition (A) for treating hair, including
- in each case converted to the undissociated succinic acid and based on the weight of the composition (A), 2 to 20% by weight, preferably 5 to 15% by weight, particularly preferably 8 to 12% by weight succinic acid, also
- at least one of the amino acids arginine, histidine or lysine and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), also
- 50 to 92% by weight, particularly preferably 60 to 87% by weight and extremely preferably 65 to 80% by weight water, in each case based on the weight of the composition (A), and
- at least one polymer A which has at least ten constituent units of formula (I)

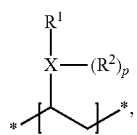

(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units,
in the composition (A) in a total amount of 0.5 to 14% by weight, preferably 1.0 to 11% by weight, particularly preferably 2.0 to 10% by weight, in each case based on the weight of the composition (A).

Another subject matter of the present invention is a composition (A) for treating hair, including in each case converted to the undissociated succinic acid and based on the weight of the composition (A), 2 to 20% by weight, preferably 5 to 15% by weight, particularly preferably 8 to 12% by weight succinic acid, also at least one of the amino acids arginine, histidine or lysine and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), also 50 to 92% by weight, particularly preferably 60 to 87% by weight and extremely preferably 65 to 80% by weight water, in each case based on the weight of the composition (A), and at least one polymer A which has at least ten constituent units of formula (I)

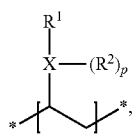
(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units and being selected from polyvinylpyrrolidone, polyvinyl alcohol and mixtures thereof, particular preference being given to polyvinylpyrrolidone,
in the composition (A) in a total amount of 0.5 to 14% by weight, preferably 1.0 to 11% by weight, particularly preferably 2.0 to 10% by weight, in each case based on the weight of the composition (A).

The polymer A included in compositions (A) which are preferred according to the invention has at least ten constituent units of formula (I)

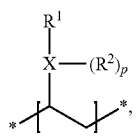
(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units.

It has surprisingly been found that a polymer A as described above and as will be explained in more detail below superbly supports the protective effect and repair effect exerted by the combination of at least one saturated dicarboxylic acid having 2 to 10 carbon atoms and/or at least one salt of said acid(s) and at least one amino acid of formula (VI), as explained above, on oxidatively colored or bleached keratin fibers.

In the context of the present invention, "polymer" will be understood to mean polymers as per the IUPAC definition, which include at least 10 identical constituent units.

According to RÖMPP Chemie Lexikon, as at July 2009, according to the IUPAC definition the term "polymer" refers to a substance which is composed of a collective of macromolecules (polymer molecules) constructed from chemical units, said macromolecules or polymer molecules differing from one another by the degree of polymerization, molecular weight and chain length. In such substances formed of so-called polymer units, therefore, all macromolecules are of identical construction and differ only in their chain length (degree of polymerization). According to this IUPAC definition, a polymer is also "a polyreaction product which is constructed from a plurality of molecules in which one type or a plurality of types of atoms or atom groups (so-called constituent units, basic building blocks or repeat units) are repeatedly lined up next to one another.

The number of constituent units in a polymer is referred to as the degree of polymerization. Polymers A and polymers B which are preferred according to the invention have in each case a degree of polymerization in the range from 40 to 1000, preferably 100 to 800, particularly preferably 350 to 650. Other polymers A having at least ten constituent units of formula (I) which are preferred according to the invention includes 40 to 1000, preferably 100 to 800, particularly preferably 350 to 650 identical constituent units of formula (I).

$R^1$ and $R^2$ preferably each independently of one another represent hydrogen or a $C_2$-$C_{10}$ acyl group which is preferably selected from an acetyl, propanoyl or n-butanoyl group, particularly preferably selected from an acetyl group.

Polymers A which are preferred according to the invention have at least 10 constituent units of formula (I), in which X represents nitrogen, the polymer A including no permanently ionic constituent units.

Other polymers A which are particularly preferred according to the invention have at least 10 constituent units of formula (I), in which X represents nitrogen and $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group.

If $R^1$ and $R^2$ together with X form a five-membered or six-membered, saturated or unsaturated ring which optionally includes further heteroatoms preferably selected from N and O, said ring is preferably substituted with at least one functional group selected from =O. One particularly preferred substituent combination X, $R^1$, $R^2$ is a pyrrolidone group, so that a constituent unit of formula (I) which is particularly preferred according to the invention is a unit of formula (Ia)

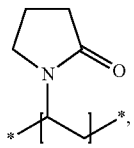

(Ia)

in which X represents nitrogen and $R^1$ and $R^2$ together with said nitrogen atom form a five-membered, saturated ring which includes no further heteroatoms and which is substituted in the 2-position with a functional group =O.

Another particularly preferred substituent combination X, $R^1$, $R^2$ is an ε-caprolactam group, so that a constituent unit of formula (I) which is particularly preferred according to the invention is a unit of formula (I b)

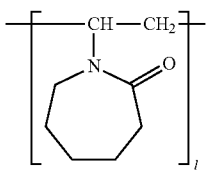

(Ib)

in which X represents nitrogen and $R^1$ and $R^2$ together with said nitrogen atom form a six-membered, saturated ring which includes no further heteroatoms and which is substituted with a functional group =O.

Another particularly preferred substituent combination X, $R^1$, $R^2$ is an imidazole group, so that another unit of formula (I) which is particularly preferred according to the invention is a unit in which X represents nitrogen and $R^1$ and $R^2$ together with said nitrogen atom form a five-membered, unsaturated ring which includes nitrogen as a further heteroatom.

Other polymers A which are preferred according to the invention include 25-100 mol %, preferably 55-100 mol %, particularly preferably 85-100 mol % constituent units of formula (I) in which X represents nitrogen, the polymer A including no permanently ionic constituent units.

Other polymers A which are preferred according to the invention include 25-100 mol %, preferably 55-100 mol %, particularly preferably 85-100 mol % constituent units of formula (I) in which X represents nitrogen and $R^1$ and $R^2$ together with X form a five-membered or six-membered, saturated or unsaturated ring which optionally includes further heteroatoms selected from N and O and is optionally substituted with at least one C1-C6 alkyl group and/or with at least one functional group, the polymer A including no permanently ionic constituent units.

Polymers A which are particularly preferred according to the invention include 98-100 mol % constituent units of formula (Ia), the polymer A including no permanently ionic constituent units.

Polymers A which are extremely preferred according to the invention include 98-100 mol % constituent units of formula (Ia) and have a degree of polymerization in the range from 40 to 1000, preferably 100 to 800, particularly preferably 350 to 650, the polymer A including no permanently ionic constituent units Particularly preferred polymers A are polyvinylpyrrolidone homopolymers having a degree of polymerization in the range from 40 to 1000, preferably 100 to 800, particularly preferably 350 to 650.

Another particularly preferred substituent combination X, $R^1$, $R^2$ is a constituent unit of formula (I) in which X represents oxygen, p is zero and $R^1$ represents hydrogen.

Another particularly preferred substituent combination X, $R^1$, $R^2$ is a constituent unit of formula (I) in which X represents oxygen, p is zero and $R^1$ represents an acetyl group.

Other polymers A which are preferred according to the invention includes 75-92 mol % constituent units of formula (I) in which X represents oxygen, p is zero and $R^1$ represents hydrogen, and 8-25 mol % constituent units of formula (I) in which X represents oxygen, p is zero and $R^1$ represents an acetyl group, the polymer A including no permanently ionic constituent units.

Other polymers A which are preferred according to the invention includes 40 to 1000, preferably 100 to 800, particularly preferably 350 to 650 constituent units of formula (I), of which 75-92 mol % constituent units of formula (I) in which X represents oxygen, p is zero and $R^1$ represents hydrogen, and 8-25 mol % constituent units of formula (I) in which X represents oxygen, p is zero and $R^1$ represents an acetyl group, the polymer A including no permanently ionic constituent units.

Other polymers A which are preferred according to the invention includes 65-25 mol % constituent units of formula (Ia) and 35-75 mol % constituent units of formula (I) in which X represents oxygen, p is zero and $R^1$ represents an acetyl group, the polymer A including no permanently ionic constituent units.

Other polymers A which are preferred according to the invention includes 40 to 1000, preferably 100 to 800, particularly preferably 350 to 650 constituent units of formula (I), of which 65-25 mol % constituent units of formula (Ia) and 35-75 mol % constituent units of formula (I) in which X represents oxygen, p is zero and $R^1$ represents an acetyl group, the polymer A including no permanently ionic constituent units.

The at least one polymer A having at least ten constituent units of formula (I) has no permanently ionic charges. However, it is possible that the constituent units of formula (I) are in ionic form, in particular in cationic form, for example due to protonation of the nitrogen atom in an acidic carrier. However, these charges are not permanent but rather are temporary since they depend on the surrounding medium.

Preferred compositions (A) according to the invention includes the at least one polymer A having at least ten constituent units of formula (I) in a total amount of 0.5 to 14% by weight, preferably 1.0 to 11% by weight, particularly preferably 2.0 to 10% by weight, in each case based on the weight of the composition (A).

Permanently Cationic Polymer B (Optional)

As a further optional ingredient, compositions (A) which are preferred according to the invention includes at least one permanently cationic polymer B.

Besides at least one permanently cationically charged monomer type, the permanently cationic polymer preferably also includes at least one permanently anionically charged monomer type, the cationic monomers being present in molar excess relative to the anionic monomers so that the at least one second polymer according to the invention has a cationic net charge. Such polymers which are preferred according to the invention are also referred to as amphoteric or zwitterionic polymers.

In a first preferred embodiment, compositions (A) which are preferred according to the invention includes at least one permanently cationic polymer selected from
cationic polymers constructed from monomers with quaternary ammonium groups of general formula (IIa),

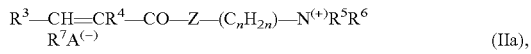

in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, preferably selected from cationic polymers constructed from acrylamidopropyl trimethylammonium chloride, particularly preferably selected from amphoteric polymers having a cationic net charge which are constructed by polymerization from c) cationic monomers with quaternary ammonium groups of general formula (IIa),

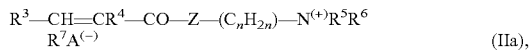

in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, and d) at least one unsaturated carboxylic acid selected from acrylic acid, methacrylic acid and crotonic acid and from mixtures of said acids, wherein the at least one unsaturated carboxylic acid may be in the form of its salts, wherein in the polymer the cationic monomers are in molar excess relative to the anionic monomers;

extremely preferably selected from amphoteric polymers having a cationic net charge which includes the at least one monomer type of general formula (IIa) and the at least one monomer type of the unsaturated carboxylic acid, selected from acrylic acid, methacrylic acid and crotonic acid and mixtures thereof, in a molar ratio of 60:40 to 95:5, preferably 75:25 to 90:10, most extremely preferably selected from amphoteric copolymers having a cationic net charge which consist of acrylamidopropyl trimethylammonium chloride and acrylic acid in a molar ratio of 60:40 to 95:5, preferably 75:25 to 90:10;

2-[2-hydroxy-3-(trimethylammonio)propoxy]ethyl cellulose ether chloride, which is obtainable for example under the INCI name Polyquaternium-10, terpolymers of acrylic acid, diallyldimethylammonium chloride and acrylamide, such as those obtainable for example under the INCI name Polyquaternium-39, homopolymers of N,N,N-trimethyl-2-[(methyl-1-oxo-2-propenyl)oxy]ethanaminium chloride, such as those obtainable for example under the INCI name Polyquaternium-37, copolymers of diallyldimethylammonium chloride and acrylic acid, such as those obtainable for example under the INCI name Polyquaternium-22, hydroxyethyl cellulose/dimethyldiallylammonium chloride copolymers, such as those obtainable for example under the INCI name Polyquaternium-4, copolymers of acrylamide and beta-methacrylyloxyethyl-trimethyl ammonium methosulfate, such as those obtainable for example under the INCI name Polyquaternium-5, homopolymers of N,N-dimethyl-N-2-propenyl-2-propen-1-aminium chloride, such as those obtainable for example under the INCI name Polyquaternium-6, copolymers of diallyldimethylammonium chloride and acrylamide, such as those obtainable for example under the INCI name Polyquaternium-7, copolymers of vinylpyrrolidone and dimethylaminoethyl methacrylate diethyl sulfate, such as those obtainable for example under the INCI name Polyquaternium-11, and mixtures of the aforementioned polymers.

Permanent cationic polymers which are extremely preferred according to the invention are selected from 2-[2-hydroxy-3-(trimethylammonio)propoxy]ethyl cellulose ether chloride, amphoteric copolymers having a cationic net charge which consist of acrylamidopropyl trimethylammonium chloride and acrylic acid in a molar ratio of 60:40 to 95:5, preferably 75:25 to 90:10, and terpolymers of acrylic acid, diallyldimethylammonium chloride and acrylamide, as well as mixtures of two or three of said polymers.

Particularly preferred polymer B mixtures includes 2-[2-hydroxy-3-(trimethylammonio)-propoxy]ethyl cellulose ether chloride and at least one amphoteric copolymer having a cationic net charge which consists of acrylamidopropyl trimethylammonium chloride and acrylic acid in a molar ratio of 60:40 to 95:5, preferably 75:25 to 90:10.

Other particularly preferred polymer B mixtures includes 2-[2-hydroxy-3-(trimethylammonio)propoxy]ethyl cellulose ether chloride, at least one amphoteric copolymer having a cationic net charge which consists of acrylamidopropyl trimethylammonium chloride and acrylic acid in a molar ratio of 60:40 to 95:5, preferably 75:25 to 90:10, and at least one terpolymer of acrylic acid, diallyldimethylammonium chloride and acrylamide.

Permanently cationic polymers B which are likewise extremely preferred according to the invention are selected from Polyquaternium-10, amphoteric copolymers having a cationic net charge which consist of acrylamidopropyl trimethylammonium chloride and acrylic acid in a molar ratio of 60:40 to 95:5, preferably 75:25 to 90:10, and Polyquaternium-39, as well as mixtures of two or three of said polymers.

Other particularly preferred polymer B mixtures includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10.

Other particularly preferred polymer B mixtures includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, and Polyquaternium-39.

Preferred compositions (A) according to the invention includes the at least one permanently cationic polymer B in a total amount of 0.1 to 5% by weight, preferably 0.2 to 3% by weight, particularly preferably 0.5 to 1.5% by weight, in each case based on the weight of the composition (A) according to the invention.

Other compositions (A) which are preferred according to the invention includes at least one permanently cationic polymer B selected from cationic polymers constructed from monomers with quaternary ammonium groups of general formula (IIa),

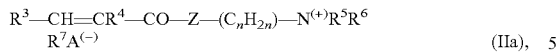 (IIa), in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, preferably selected from cationic polymers constructed from acrylamidopropyl trimethylammonium chloride, particularly preferably selected from amphoteric polymers having a cationic net charge which are constructed by polymerization from e) cationic monomers with quaternary ammonium groups of general formula (IIa),

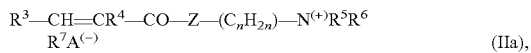 (IIa), in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, and f) at least one unsaturated carboxylic acid selected from acrylic acid, methacrylic acid and crotonic acid and from mixtures of said acids, wherein the at least one unsaturated carboxylic acid may be in the form of its salts, wherein in the polymer the totality of all the cationic monomers is in molar excess relative to the totality of all the anionic monomers;

extremely preferably selected from amphoteric polymers having a cationic net charge which includes the at least one monomer type of general formula (IIa) and the at least one monomer type of the unsaturated carboxylic acid, selected from acrylic acid, methacrylic acid and crotonic acid and mixtures thereof, in a molar ratio of 60:40 to 95:5, preferably 75:25 to 90:10, most extremely preferably selected from amphoteric copolymers having a cationic net charge which consist of acrylamidopropyl trimethylammonium chloride and acrylic acid in a molar ratio of 60:40 to 95:5, preferably 75:25 to 90:10;

2-[2-hydroxy-3-(trimethylammonio)propoxy]ethyl cellulose ether chloride, which is obtainable for example under the INCI name Polyquaternium-10, terpolymers of acrylic acid, diallyldimethylammonium chloride and acrylamide, such as those obtainable for example under the INCI name Polyquaternium-39, homopolymers of N,N,N-trimethyl-2-[(methyl-1-oxo-2-propenyl)oxy]ethanaminium chloride, such as those obtainable for example under the INCI name Polyquaternium-37, copolymers of diallyldimethylammonium chloride and acrylic acid, such as those obtainable for example under the INCI name Polyquaternium-22, hydroxyethyl cellulose/dimethyldiallylammonium chloride copolymers, such as those obtainable for example under the INCI name Polyquaternium-4, copolymers of acrylamide and beta-methacrylyloxyethyltrimethyl ammonium methosulfate, such as those obtainable for example under the INCI name Polyquaternium-5, homopolymers of N,N-dimethyl-N-2-propenyl-2-propen-1-aminium chloride, such as those obtainable for example under the INCI name Polyquaternium-6, copolymers of diallyldimethylammonium chloride and acrylamide, such as those obtainable for example under the INCI name Polyquaternium-7, copolymers of vinylpyrrolidone and dimethylaminoethyl methacrylate diethyl sulfate, such as those obtainable for example under the INCI name Polyquaternium-11, in a total amount of 0.1 to 5% by weight, preferably 0.2 to 3% by weight, particularly preferably 0.5 to 1.5% by weight, in each case based on the weight of the composition (A) according to the invention.

Other compositions (A) which are preferred according to the invention includes 2-[2-hydroxy-3-(trimethylammonio)propoxy]ethyl cellulose ether chloride and at least one amphoteric copolymer having a cationic net charge which consists of acrylamidopropyl trimethylammonium chloride and acrylic acid in a molar ratio of 60:40 to 95:5, preferably 75:25 to 90:10, in a total amount of 0.1 to 5% by weight, preferably 0.2 to 3% by weight, particularly preferably 0.5 to 1.5% by weight, in each case based on the weight of the composition (A) according to the invention.

Other compositions (A) which are preferred according to the invention includes 2-[2-hydroxy-3-(trimethylammonio)propoxy]ethyl cellulose ether chloride, at least one amphoteric copolymer having a cationic net charge which consists of acrylamidopropyl trimethylammonium chloride and acrylic acid in a molar ratio of 60:40 to 95:5, preferably 75:25 to 90:10, and at least one terpolymer of acrylic acid, diallyldimethylammonium chloride and acrylamide, in a total amount of 0.1 to 5% by weight, preferably 0.2 to 3% by weight, particularly preferably 0.5 to 1.5% by weight, in each case based on the weight of the composition (A) according to the invention.

Other compositions (A) which are particularly preferred according to the invention includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, in a total amount of 0.1 to 5% by weight, preferably 0.2 to 3% by weight, particularly preferably 0.5 to 1.5% by weight, in each case based on the weight of the composition (A) according to the invention.

Other compositions (A) which are particularly preferred according to the invention includes Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, and Polyquaternium-39, in a total amount of 0.1 to 5% by weight, preferably 0.2 to 3% by weight, particularly preferably 0.5 to 1.5% by weight, in each case based on the weight of the composition (A) according to the invention.

Optionally, the aforementioned composition (A) may also includes at least one substance selected from compounds of general formula (III)

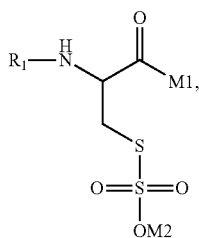

(III)

wherein

R1 represents a hydrogen atom or a structural element of formula (IV)

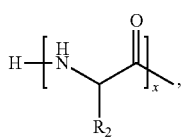

(IV)

wherein x represents an integer from 1 to 100, the radical R2 in each of the structural elements of formula (IV) can in each case be selected independently of the preceding structural element of formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 represents the group —OM2 or a structural element of formula (V)

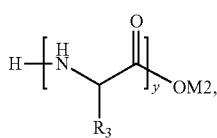

(V)

wherein y represents an integer from 1 to 100, the radical R3 in each of the structural elements of formula (V) can in each case be selected independently of the preceding structural element of formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 represents a hydrogen atom, an equivalent of a monovalent or polyvalent cation or an ammonium ion $(NH_4)^+$.

In one very particularly preferred embodiment, a composition (A) according to the invention is characterized in that it includes at least one compound of formula (III) which has a molecular weight $M_w$ of 200 to 2000 Da (Dalton), preferably 250 to 1500 Da, more preferably 300 to 1200 Da, in particular 400 to 800 Da.

If a mixture of oligomers is used in the composition (A) according to the invention, these mixtures can be defined by their average molecular weight.

In this case, a composition (A) which is preferred according to the invention is characterized in that it includes at least one mixture of compounds of formula (III) which has an average molecular weight $M_w$ of 200 to 2000 Da, preferably 250 to 1500 Da, more preferably 300 to 1200 Da, in particular 400 to 800 Da.

It has also been found that the protective effect or repair effect exhibited by the compounds of formula (III) also depends on the repeat indices x and y. As described above, it is very particularly preferred if x represents an integer from 1 to 10 and y represents an integer from 1 to 10.

In another very particularly preferred embodiment, a composition (A) according to the invention is characterized in that it includes at least one compound of formula (III), wherein R1 represents a structural element of formula (IV), and M1 represents a structural element of formula (V), and x represents an integer from 1 to 10 and y represents an integer from 1 to 10.

Besides the molecular weight of the compound of formula (III), the amount of Bunte salt units included in the compound of formula (III) also has a critical influence on the efficacy of the protective effect or "repair effect" of the compounds.

Compounds having at least one Bunte salt unit—as is present for example in the compound of formula (IIIa)—are very effective, particularly when they are used as a monomeric compound. Oligopeptides having at least one Bunte salt unit are particularly effective when they have a low molecular weight of up to 1200, in particular 800 Dalton.

When using oligopeptides, however, it is of very particular advantage if the compound of formula (III) has at least two, preferably at least three Bunte salt units.

In another very particularly preferred embodiment, a composition (A) according to the invention is characterized in that it includes at least one compound of formula (III), wherein R1 represents a structural element of formula (IV), and the radical R2 in at least one structural element of formula (IV) represents a (sulfosulfanyl)methyl group (that is to say a group HO—$S(O_2)$—S—$CH_2$—).

In another very particularly preferred embodiment, a composition (A) according to the invention is characterized in that it includes at least one compound of formula (III), wherein R1 represents a structural element of formula (IV), and
x represents an integer of at least 3 and
the radical R2 in at least 3 structural elements of formula (IV) represents a 2-carboxyethyl group (that is to say a group HOOC—CH2-CH2-).

In another very particularly preferred embodiment, a composition (A) according to the invention is characterized in that it includes at least one compound of formula (III), wherein M1 represents a structural element of formula (V), and
y represents an integer of at least 3 and
the radical R3 in at least 3 structural elements of formula (IV) represents a group (Glu).

The at least one compound of formula (III) is included in a total amount of 0.001 to 10% by weight, based on the total weight of the composition (A) preferred according to the invention. However, it has surprisingly been found that the compound(s) of formula (III) can bring about a very good reduction in damage to the hair even when used in low concentrations. This is particularly advantageous because the at least one compound of formula (III) is to be added to the composition (A) according to the invention as an additive (for example in the form of a care solution or repair solution) prior to application to the hair. For this reason, it is particularly advantageous if the composition (A) preferred according to the invention includes one or more compounds of the above formula (III) in a total amount of 0.001 to 2.5% by weight, more preferably 0.01 to 1.0% by weight and particularly preferably 0.02 to 0.1% by weight, in each case based on the weight of the composition (A) according to the invention.

In another very particularly preferred embodiment, a composition (A) according to the invention is characterized in that it includes one or more compounds of the above formula (III) in a total amount of 0.001 to 2.5% by weight, more preferably 0.01 to 1.0% by weight and particularly preferably 0.02 to 0.1% by weight, in each case based on the weight of the composition (A) according to the invention, wherein, in formula (III), R1 represents a structural element of formula (IV) and the radical R2 in at least one structural element of formula (IV) represents a (sulfosulfanyl)methyl group (that is to say a group HO—S(O2)—S—CH2—).

It may also be preferred according to the invention initially to store the hair-protecting combination according to the invention, consisting of at least one saturated dicarboxylic acid having 2 to 10 carbon atoms and at least one amino acid of formula (VI), together with the preparation which includes the at least one alkalizing agent and optionally at least one oxidation dye precursor and/or at least one substantive dye, but separately from the oxidizing agent preparation which includes at least one peroxide compound, and to produce the coloring or bleaching agent according to the invention or preferred according to the invention by mixing the two components just before starting the method according to the invention or preferred according to the invention for the oxidative coloring and/or lightening of keratin fibers.

In another very particularly preferred embodiment, the composition (A) according to the invention has a pH in the range from 3.5 to 7.1, preferably 4.5 to 6.5, particularly preferably 5.0 to 6.0, in each case measured at 20° C.

Another subject matter of the present invention is therefore a method for the oxidative coloring and/or lightening of keratin fibers, in particular of human hair, which includes the following method steps:

I. providing a composition (AB), including
a) at least one saturated dicarboxylic acid having 2 to 10 carbon atoms and/or at least one salt of said acid(s),
b) at least one amino acid of formula (VI)

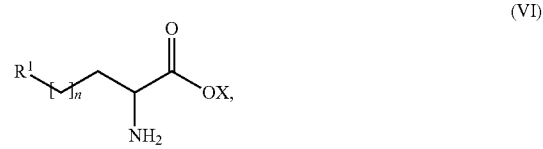

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
the amino acid of formula (VI) preferably being selected from arginine, lysine, histidine and mixtures thereof, particularly preferably mixtures of arginine and lysine, or at least one salt of said amino acids,
c) optionally also at least one substance selected from compounds of general formula (III)

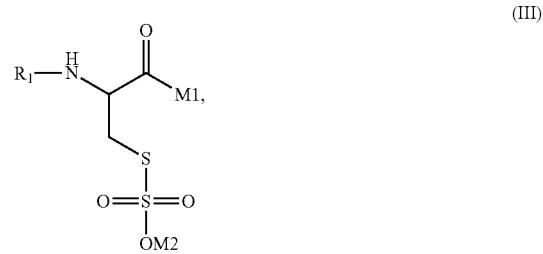

wherein
R1 represents a hydrogen atom or a structural element of formula (IV)

wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 represents the group —OM2 or a structural element of formula (V)

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$, and
polymers A which have at least ten constituent units of formula (I)

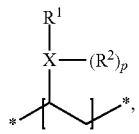

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units, d) at least one alkalizing agent, selected from ammonium hydroxide, monoethanolamine and sodium silicates, and mixtures thereof,
e) water, and
f) optionally at least one oxidation dye precursor and/or at least one substantive dye,
II. providing a composition (C), including
g) at least one peroxide compound, which is preferably hydrogen peroxide,
III. mixing compositions (AB) and (C) with one another, then immediately
IV. applying the mixture of (AB) and (C) to the keratin fibers, in particular to the human hair, and
V. rinsing out after a leave-in time of 0.1 to 60 minutes, preferably 1 to 45 minutes, particularly preferably 10 to 30 minutes,
VI. optionally further hair treatments, such as styling, conditioning and/or drying.

Mixing Ratios of Composition (AB) with Composition (C)

It has proven to be effective according to the invention if the weight ratio of composition (AB), which includes the hair-protecting combination consisting of at least one polymer which has at least ten constituent units of formula (I), also at least one permanently cationic polymer, at least one amino acid and water, in the alkalizing composition (B) including at least one alkalizing agent and optionally oxidation dye precursors and/or substantive dyes, and composition (C), including at least one peroxide compound, is in the range of [weight of AB]/[weight of C] 1:0.8 to 1:2.5, preferably 1:1 to 1:2.

Coloring or lightening methods which are preferred according to the invention and which use the at least two aforementioned compositions (AB) and (C) are characterized in that the at least one dicarboxylic acid having 2 to 10 carbon atoms, preferably being selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, is included in the composition (AB) in a total amount of 0.03 to 7% by weight, preferably 0.1 to 5% by weight, particularly preferably 0.5 to 3% by weight, very particularly preferably 0.9 to 1.5% by weight, in each case converted to the undissociated dicarboxylic acid and based on the weight of the composition (AB).

Coloring or lightening methods which are preferred according to the invention and which use the at least two aforementioned compositions (AB) and (C) are characterized in that the at least one polymer A having at least ten constituent units of formula (I) is included in the composition (AB) in a total amount of 0.8 to 10% by weight, preferably 2 to 6% by weight, particularly preferably 3 to 5% by weight, in each case based on the weight of the composition (AB).

Coloring or lightening methods which are preferred according to the invention and which use the at least two aforementioned compositions (AB) and (C) are also characterized in that the at least one permanently cationic polymer B is included in the composition (AB) in a total amount of 0.1 to 5% by weight, preferably 0.2 to 3.0% by weight, particularly preferably 0.4 to 1.5% by weight, in each case based on the weight of the composition (AB).

Coloring or lightening methods which are preferred according to the invention and which use the at least two aforementioned compositions (AB) and (C) are also characterized in that the at least one amino acid is included in the composition (AB) in a total amount of 0.5 to 8% by weight, preferably 0.9 to 5% by weight, particularly preferably 2 to 3% by weight, in each case based on the weight of the composition (AB).

Other coloring or lightening methods which are preferred according to the invention and which use the at least two aforementioned compositions (AB) and (C) are characterized in that a mixture of serine and at least one of the basic amino acids arginine, histidine or lysine is included in the composition (AB) in a total amount of 0.5 to 8% by weight, preferably 0.9 to 5% by weight, particularly preferably 2 to 3% by weight, in each case converted to the mass of the free amino acid and based on the weight of the composition (AB), said composition particularly preferably including serine and at least one of the basic amino acids arginine, histidine or lysine in a molar ratio of serine to total basic amino acids in the range from 1:1 to 50:1, preferably 5:1 to 30:1.

Other coloring or lightening methods which are preferred according to the invention and which use the at least two aforementioned compositions (AB) and (C) are characterized in that one or more compounds of the above formula (III) are included in the composition (AB) in a total amount of 0.002 to 2.5% by weight, more preferably 0.02 to 2.0% by weight and particularly preferably 0.04 to 0.2% by weight, in each case based on the weight of the composition (AB).

Other coloring or lightening methods which are preferred according to the invention and which use the at least two aforementioned compositions (AB) and (C) are characterized in that the composition (C) includes 1.0 to 23.0% by weight, more preferably 2.5 to 21.0% by weight, particularly preferably 4.0 to 20.0% by weight and very particularly preferably 5.0 to 18.0% by weight hydrogen peroxide (calculated as 100% strength $H_2O_2$), in each case based on the weight of the composition (C).

The compositions (AB) according to the invention includes water, namely preferably in an amount of 20 to 85% by weight, preferably 30 to 80% by weight, in each case based on the total weight of the composition (AB) according to the invention.

The compositions (AB) according to the invention preferably have a pH in the range from 6.5 to 10.5, preferably 8 to 10, particularly preferably 8.5 to 9.5, in each case measured at 20° C.

For the method according to the invention for the oxidative coloring and/or lightening of keratin fibers, in particular of human hair, using the at least two aforementioned compositions (AB) and (C), and the preferred embodiments thereof, what has been stated above in relation to the coloring and bleaching agents according to the invention and preferred according to the invention applies, mutatis mutandis, apart from the modified stated quantities mentioned above.

To sum up, the present invention is characterized in particular by the following points:
1. An oxidative coloring or bleaching agent for keratin fibers, in particular for human hair, including
   a) at least one saturated dicarboxylic acid having 2 to 10 carbon atoms and/or at least one salt of said acid(s),
   b) at least one amino acid of formula (VI)

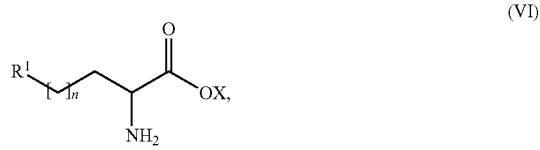

(VI)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
   c) also at least one alkalizing agent, selected from ammonium hydroxide, monoethanolamine and sodium silicates, and mixtures thereof,
   d) optionally at least one oxidation dye precursor and/or at least one substantive dye,
   e) water, and
   f) at least one peroxide compound.
2. The coloring or bleaching agent according to point 1, characterized in that the at least one saturated dicarboxylic acid having 2 to 10 carbon atoms is selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, preferably selected from succinic acid.
3. The coloring or bleaching agent according to point 1 or 2, characterized in that the at least one saturated dicarboxylic acid having 2 to 10 carbon atoms is included in a total amount of 0.2 to 4% by weight, preferably 0.33 to 3% by weight, particularly preferably 0.5 to 2% by weight, in each case converted to the undissociated dicarboxylic acid and based on the weight of the coloring or bleaching agent.
4. The coloring or bleaching agent according to any of points 1 to 3, characterized in that the at least one amino acid of formula (VI) is selected from arginine, lysine, histidine, asparagine, glutamine, cysteine, methionine, tryptophan and mixtures thereof, particularly preferably mixtures of arginine and lysine.
5. The coloring or bleaching agent according to any of points 1 to 4, characterized in that the at least one amino acid of formula (VI) is included in a total amount of 0.05 to 3% by weight, preferably 0.1 to 2% by weight, particularly preferably 0.2 to 1.2% by weight, in each case converted to the undissociated amino acid and based on the weight of the coloring or bleaching agent.
6. The coloring or bleaching agent according to any of points 1 to 4, characterized in that mixtures of arginine and lysine or at least one salt of said amino acids are included in a total amount of 0.05 to 3% by weight, preferably 0.1 to 2% by weight, particularly preferably 0.2 to 1.2% by weight, in each case converted to the undissociated amino acid and based on the weight of the coloring or bleaching agent.

7. The coloring or bleaching agent according to any of points 1 to 6, characterized in that it includes at least one compound of general formula (III)

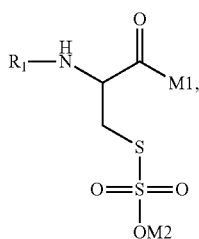

wherein
R1 represents a hydrogen atom or a structural element of formula (IV)

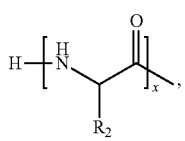

wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

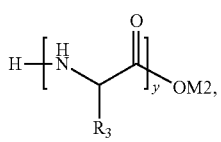

wherein
y represents an integer from 1 to 100,
the radical R3 in each of the structural elements of formula (V) can in each case be selected independently of the preceding structural element of formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$,
wherein preferably one or more compounds of the above formula (III) are included in a total amount of 0.001 to 2.5% by weight, more preferably 0.01 to 1.0% by weight and particularly preferably 0.02 to 0.1% by weight, in each case based on the weight of the coloring or bleaching agent according to the invention.

8. The coloring or bleaching agent according to any of points 1 to 7, characterized in that it includes 20 to 85% by weight, preferably 30 to 80% by weight water, in each case based on the total weight of the coloring or bleaching agent according to the invention.

9. The coloring or bleaching agent according to any of points 1 to 8, characterized in that it includes hydrogen peroxide as the peroxide compound.

10. The coloring or bleaching agent according to any of points 1 to 9, characterized in that it includes 0.5 to 13% by weight, more preferably 1 to 7% by weight, particularly preferably 2 to 6% by weight and very particularly preferably 3 to 4.5% by weight hydrogen peroxide (calculated as 100% strength $H_2O_2$), in each case based on the total weight of the coloring or bleaching agent according to the invention.

11. The coloring or bleaching agent according to any of points 1 to 10, characterized in that it includes at least one polymer A which has at least ten constituent units of formula (I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units,
wherein the at least one polymer A having at least ten constituent units of formula (I) is preferably included in a total amount of 0.2 to 5% by weight, particularly preferably 0.5 to 3% by weight, extremely preferably 1.0 to 2.3% by weight, in each case based on the weight of the coloring or bleaching agent.

12. The coloring or bleaching agent according to point 11, characterized in that the at least one polymer A having at least ten constituent units of formula (I) is selected from polymers which include 98-100 mol % constituent units of formula (Ia)

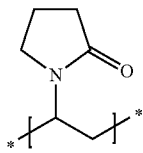

(Ia)

and have a degree of polymerization in the range from 40 to 1000, preferably 100 to 800, particularly preferably 350 to 650, the polymer A including no permanently ionic constituent units.

13. A method for the oxidative coloring and/or lightening of keratin fibers, in particular of human hair, in which a coloring or bleaching agent according to any of points 1 to 12 is applied to the keratin fibers, in particular to the human hair, and is rinsed out again after a leave-in time of 0.1 to 60 minutes, preferably 1 to 45 minutes, particularly preferably 10 to 30 minutes.

14. A method for the oxidative coloring and/or lightening of keratin fibers, in particular of human hair, which includes the following method steps:

I. providing a composition (A), including a) at least one saturated dicarboxylic acid having 2 to 10 carbon atoms and/or at least one salt of said acid(s), b) at least one amino acid of formula (VI)

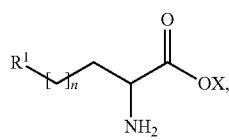

(VI)

in which
X represents a hydrogen atom or a monovalent or divalent cation;
n represents zero, 1, 2 or 3;
R1 represents a radical selected from an amino group, a guanidine group, a (1H-imidazol-4-yl) group, a carboxamide group —CONH$_2$, a 1H-indol-3-yl group, a thiol group —SH and a methylsulfanyl group —SCH$_3$, or at least one salt of said amino acid, c) water, and
d) optionally also at least one substance selected from compounds of general formula (III)

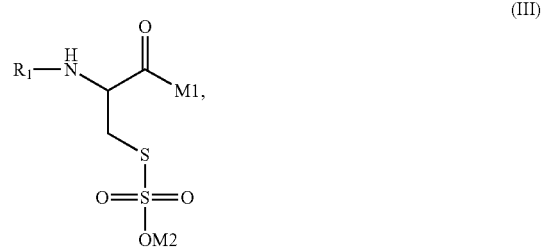

(III)

wherein
R1 represents a hydrogen atom or a structural element of formula (IV)

(IV)

wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

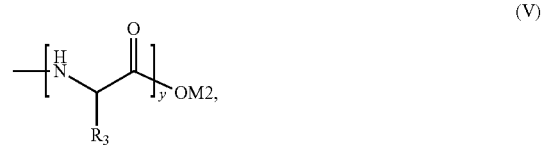

(V)

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 represents a hydrogen atom, an equivalent of a monovalent or polyvalent cation or an ammonium ion $(NH_4)^+$, and polymers A which have at least ten constituent units of formula (I)

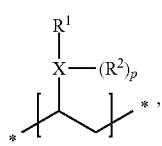
(I)

in which

X represents nitrogen or oxygen and $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and p=0 when X represents oxygen and p=1 when X represents nitrogen, the polymer A including no permanently ionic constituent units, wherein the composition (A) preferably has a pH in the range from 3.5 to 7.1, preferably 4.5 to 6.5, particularly preferably 5.0 to 6.0, in each case measured at 20° C., II. providing a composition (B), including e) at least one alkalizing agent, selected from ammonium hydroxide, monoethanolamine and sodium silicates, and mixtures thereof, f) optionally water, and g) optionally at least one oxidation dye precursor and/or at least one substantive dye, III. providing a composition (C), including h) at least one peroxide compound, which is preferably hydrogen peroxide, IV. mixing compositions (A), (B) and (C) with one another, then immediately V. applying the mixture of (A), (B) and (C) to the keratin fibers, in particular to the human hair, and VI. rinsing out after a leave-in time of 0.1 to 60 minutes, preferably 1 to 45 minutes, particularly preferably 10 to 30 minutes, VII. optionally further hair treatments, such as styling, conditioning and/or drying.

15. A composition (A), including at least one saturated dicarboxylic acid having 2 to 10 carbon atoms in a total amount of 2 to 20% by weight, preferably 5 to 15% by weight, particularly preferably 8 to 12% by weight, in each case converted to the undissociated dicarboxylic acid and based on the weight of the composition (A), the dicarboxylic acid preferably being selected from succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, oxaloacetic acid, and mixtures of said acids, extreme preference being given to succinic acid, and at least one amino acid of formula (VI) and/or a salt thereof in a total amount of 0.4 to 7.0% by weight, preferably 0.8 to 5.0% by weight, particularly preferably 1.5 to 4.0% by weight, in each case converted to the undissociated amino acid and based on the weight of the composition (A), wherein preferably at least one of the amino acids arginine, histidine or lysine and/or a salt thereof is included in a total amount of 0.4 to 7.0% by weight, preferably 0.8 to 5.0% by weight, particularly preferably 1.5 to 4.0% by weight, in each case converted to the undissociated acid and based on the weight of the composition (A), and water, preferably in an amount of 50 to 92% by weight, particularly preferably 60 to 87% by weight and extremely preferably 65 to 80% by weight, in each case based on the weight of the composition (A), optionally also at least one polymer A which has at least ten constituent units of formula (I)

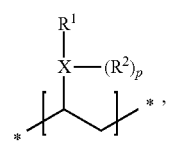
(I)

in which

X represents nitrogen or oxygen and $R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and p=0 when X represents oxygen and p=1 when X represents nitrogen, the polymer A including no permanently ionic constituent units, wherein preferably the at least one polymer A is included in a total amount of 0.5 to 14% by weight, preferably 1.0 to 11% by weight, particularly preferably 2.0 to 10% by weight, in each case based on the weight of the composition (A), wherein the composition (A) preferably has a pH in the range from 3.5 to 7.1, preferably 4.5 to 6.5, particularly preferably 5.0 to 6.0, in each case measured at 20° C.

16. A method for the oxidative coloring and/or lightening of keratin fibers, in particular of human hair, which includes the following method steps:

I. providing a composition (AB), including
a) at least one saturated dicarboxylic acid having 2 to 10 carbon atoms and/or at least one salt of said acid(s),
b) at least one amino acid of formula (VI)

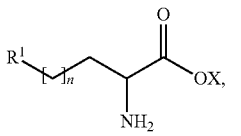
(VI)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
the amino acid of formula (VI) preferably being selected from arginine, lysine, histidine and mixtures thereof, particularly preferably mixtures of arginine and lysine, or at least one salt of said amino acids,
c) optionally also at least one substance selected from compounds of general formula (III)

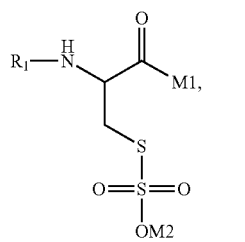
(III)

wherein
R1 represents a hydrogen atom or a structural element of formula (IV)

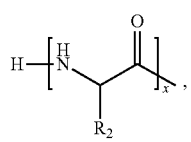
(IV)

wherein
x represents an integer from 1 to 100,
the radical R2 in each of the structural elements of formula (IV) can in each case be selected independently of the preceding structural element of formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

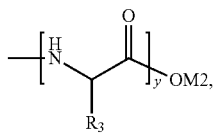
(V)

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$, and
polymers A which have at least ten constituent units of formula (I)

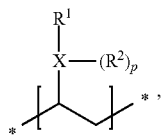
(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units, d) at least one alkalizing agent, selected from ammonium hydroxide, monoethanolamine and sodium silicates, and mixtures thereof,
e) water, and
f) optionally at least one oxidation dye precursor and/or at least one substantive dye, II. providing a composition (C), including
   g) at least one peroxide compound, which is preferably hydrogen peroxide,
III. mixing compositions (AB) and (C) with one another, then immediately
IV. applying the mixture of (AB) and (C) to the keratin fibers, in particular to the human hair, and
V. rinsing out after a leave-in time of 0.1 to 60 minutes, preferably 1 to 45 minutes, particularly preferably 10 to 30 minutes,
VI. optionally further hair treatments, such as styling, conditioning and/or drying.

17. The method according to point 14 or 16, characterized in that the at least one saturated dicarboxylic acid having 2 to 10 carbon atoms is selected from succinic acid.

18. The method according to point 14 or 16, characterized in that the at least one saturated dicarboxylic acid having 2 to 10 carbon atoms is selected from malic acid.

19. The coloring or bleaching agent according to any of points 11 or 12 or the method according to any of points 14, 16, 17 or 18 or the composition (A) according to point 12, characterized in that the at least one polymer (A) which has at least ten constituent units of formula (I) and which includes no permanently ionic constituent units is selected from polyvinylpyrrolidone, polyvinyl alcohol and mixtures thereof, particular preference being given to polyvinylpyrrolidone.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oxidative coloring or bleaching agent for keratin fibers, in particular for human hair, including
   a) at least one saturated dicarboxylic acid having 2 to 10 carbon atoms and/or a salt thereof,
   b) at least one amino acid of formula (VI)

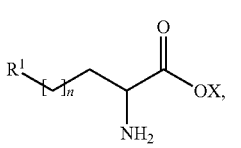

(VI)

in which
X represents a hydrogen atom or a monovalent or divalent cation;
n represents zero, 1, 2 or 3;

$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid,
c) at least one alkalizing agent selected from the group consisting of ammonium hydroxide, monoethanolamine, and sodium silicates,
d) optionally at least one oxidation dye precursor and/or at least one substantive dye,
e) water,
f) at least one peroxide compound, and
g) at least one oligomer of general formula (III) having a molecular weight of 200 to 2000 Dalton

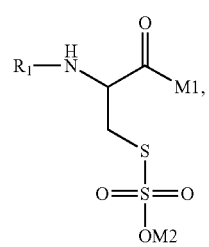

(III)

wherein
R1 represents a hydrogen atom or a structural element of formula (IV)

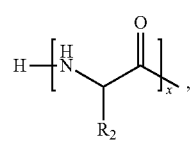

(IV)

wherein
x represents an integer from 1 to 100,
each R2 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

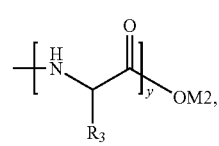

(V)

wherein
y represents an integer from 1 to 100,
each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 represents a hydrogen atom, an equivalent of a monovalent or polyvalent cation or an ammonium ion (NH4)⁺.

2. The coloring or bleaching agent according to claim 1, wherein the at least one saturated dicarboxylic acid having 2 to 10 carbon atoms is/are selected from the group consisting of succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, and oxaloacetic acid.

3. The coloring or bleaching agent according to claim 2, wherein the at least one saturated dicarboxylic acid having 2 to 10 carbon atoms is/are selected from the group consisting of succinic acid and malic acid.

4. The coloring or bleaching agent according to claim 1, wherein the at least one saturated dicarboxylic acid having 2 to 10 carbon atoms is included in a total amount of 0.2 to 4% by weight, as converted to the undissociated dicarboxylic acid and based on the weight of the coloring or bleaching agent.

5. The coloring or bleaching agent according to claim 1, wherein the at least one amino acid of formula (VI) is/are selected from the group consisting of arginine, lysine, histidine, asparagine, glutamine, cysteine, methionine, and tryptophan.

6. The coloring or bleaching agent according to claim 1, wherein the at least one amino acid of formula (VI) is a mixture of arginine and lysine.

7. The coloring or bleaching agent according to claim 1, wherein the at least one amino acid of formula (VI) is included in a total amount of 0.05 to 3% by weight as converted to the undissociated amino acid and based on the weight of the coloring or bleaching agent.

8. The coloring or bleaching agent according to claim 1, wherein
one or more compounds of formula (III) are included in a total amount of 0.001 to 2.5% by weight in each case based on the weight of the coloring or bleaching agent.

9. The coloring or bleaching agent according to claim 1, wherein the agent includes hydrogen peroxide as the peroxide compound.

10. The coloring or bleaching agent according to claim 1, wherein the agent further includes at least one polymer A which has at least ten constituent units of formula (I)

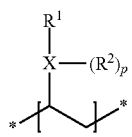

(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms selected from N and O, and/or is optionally substituted with at least one C1-C6 alkyl group and/or with at least one functional group, and
p=0 when X represents oxygen and p=1 when X represents nitrogen,
the polymer A including no permanently ionic constituent units,
wherein the at least one polymer A having at least ten constituent units of formula (I) is included in a total amount of 0.2 to 5% by weight based on the weight of the coloring or bleaching agent.

11. The coloring or bleaching agent according to claim 10, wherein the at least one polymer A at least ten constituent units of formula (I) is selected from the group consisting of polymers which include 98-100 mol % constituent units of formula (Ia)

(Ia)

and have a degree of polymerization in the range from 40 to 1000, the polymer A including no permanently ionic constituent units.

12. A method for the oxidative coloring and/or lightening of keratin fibers, including applying a coloring or bleaching agent according to claim 1 to the keratin fibers, and rinsing the agent out again after a leave-in time of 0.1 to 60 minutes.

13. A method for the oxidative coloring and/or lightening of keratin fibers, including:
I. providing a composition (A), including
a) at least one saturated dicarboxylic acid having 2 to 10 carbon atoms and/or at least one salt of the acid(s),
b) at least one amino acid of formula (VI)

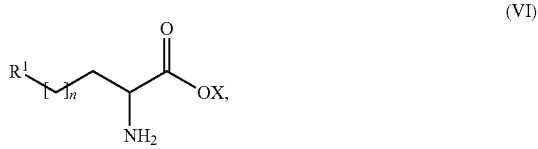

(VI)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —CONH₂, a 1H-indol-3-yl group, a thiol group —SH and a methylsulfanyl group —SCH₃, or at least one salt of the amino acid(s),
c) water, and
d) at least one oligomer of general formula (III) having a molecular weight of 200 to 2000 Dalton

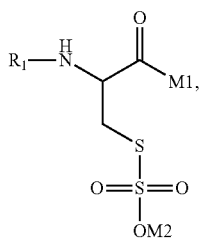

wherein
R1 represents a hydrogen atom or a structural element of formula (IV)

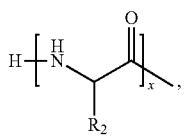

wherein
x represents an integer from 1 to 100,
each R2 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

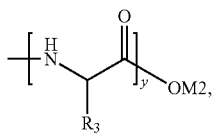

wherein
y represents an integer from 1 to 100,
each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$, and
polymers A which have at least ten constituent units of formula (I)

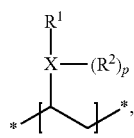

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms selected from N and O, and/or is optionally substituted with at least one C1-C6 alkyl group and/or with at least one functional group, and
p=0 when X represents oxygen and p=1 when X represents nitrogen, the polymer A including no permanently ionic constituent units,
wherein the composition (A) has a pH in the range from 3.5 to 7.1 at 20° C.,
II. providing a composition (B), including
e) at least one alkalizing agent, selected from the group consisting of ammonium hydroxide, monoethanolamine and sodium silicates, and mixtures thereof,
f) optionally water, and
g) optionally at least one oxidation dye precursor and/or at least one substantive dye, wherein the composition (B) has a pH in the range from 6.5 to 11.0 at 20° C.,
III. providing a composition (C), including
h) at least one peroxide compound wherein the composition (C) has a pH in the range from 2.5 to 6.5 at 20° C.,
IV. mixing compositions (A), (B) and (C) with one another, then immediately
V. applying the mixture of (A), (B) and (C) to the keratin fibers,
VI. rinsing out after a leave-in time of 0.1 to 60 minutes, and
VII. optionally performing further hair styling, conditioning and/or drying treatments.

14. A composition (A), including
at least one saturated dicarboxylic acid having 2 to 10 carbon atoms in a total amount of 2 to 20% by weight as converted to the undissociated dicarboxylic acid and based on the weight of the composition (A), the dicarboxylic acid(s) being selected from the group consisting of succinic acid, malic acid, oxalic acid, malonic acid, adipic acid, pimelic acid, suberic acid, azelaic acid, sebacic acid, D-tartaric acid, L-tartaric acid, mesotartaric acid, racemic tartaric acid, alpha-ketoglutaric acid, beta-ketoglutaric acid, and oxaloacetic acid,
at least one amino acid of formula (VI) and/or a salt thereof in a total amount of 0.4 to 7.0% by weight as converted to the undissociated amino acid and based on the weight of the composition (A),

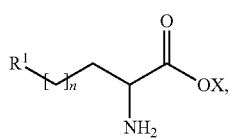

in which

X represents a hydrogen atom or a monovalent or divalent cation;

n represents zero, 1, 2 or 3;

R¹ represents a radical selected from an amino group, a guanidine group, a (1H-imidazol-4-yl) group, a carboxamide group —CONH₂, a 1H-indol-3-yl group, a thiol group —SH and a methylsulfanyl group —SCH₃, or at least one salt of said amino acid, and water, in an amount of 50 to 92% based on the weight of the composition (A), optionally also at least one polymer A which has at least ten constituent units of formula (I)

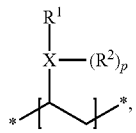

(I)

in which

X represents nitrogen or oxygen and

R¹ and R² in each case independently of one another represent hydrogen or a C2-C10 acyl group or R¹ and R² together with X form a five-membered or six-membered, saturated or unsaturated ring which optionally includes further heteroatoms selected from N and O, and/or is optionally substituted with at least one C1-C6 alkyl group and/or with at least one functional group, and p=0 when X represents oxygen and p=1 when X represents nitrogen, the polymer A including no permanently ionic constituent units, wherein the at least one polymer A is included in a total amount of 0.5 to 14% based on the weight of the composition (A), and at least one oligomer of general formula (III) having a molecular weight of 200 to 2000 Dalton

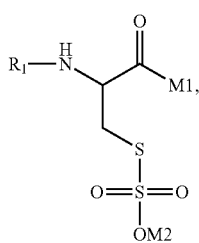

(III)

wherein

R1 represents a hydrogen atom or a structural element of formula (IV)

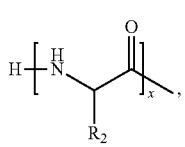

(IV)

wherein x represents an integer from 1 to 100, each R2 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M1 represents the group —OM2 or a structural element of formula (V)

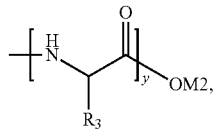

(V)

wherein y represents an integer from 1 to 100, each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, M2 represents a hydrogen atom, an equivalent of a monovalent or polyvalent cation or an ammonium ion (NH₄)⁺, and wherein the composition (A) has a pH in the range from 3.5 to 7.1 at 20° C.

15. The method according to claim 14, wherein the at least one amino acid of formula (VI) includes at least one of arginine, histidine, lysine and a salt thereof as converted to the undissociated amino acid.

16. A method for the oxidative coloring and/or lightening of keratin fibers, in particular of human hair, which includes the following method steps:

I. providing a composition (AB), including
a) at least one saturated dicarboxylic acid having 2 to 10 carbon atoms and/or at least one salt of the acid(s),
b) at least one amino acid of formula (VI)

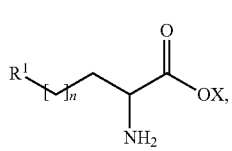

(VI)

in which

X represents a hydrogen atom or a monovalent or divalent cation;

n represents zero, 1, 2 or 3;

R¹ represents a radical selected from an amino group, a guanidine group, a (1H-imidazol-4-yl) group, a carboxamide group —CONH₂, a 1H-indol-3-yl group, a thiol group —SH and a methylsulfanyl group —SCH₃, or at least one salt of the amino acid, at least one oligomer of general formula (III) having a molecular weight of 200 to 2000 Dalton

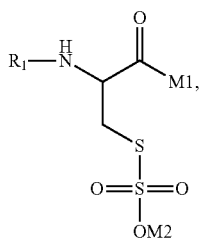
(III)

R¹ represents a hydrogen atom or a structural element of formula (IV)

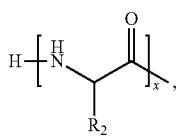
(IV)

wherein
x represents an integer from 1 to 100,
each R2 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

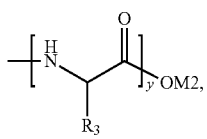
(V)

wherein
y represents an integer from 1 to 100,
each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, and M2 represents a hydrogen atom, an equivalent of a monovalent or polyvalent cation or an ammonium ion (NH4)⁺, and polymers A which have at least ten constituent units of formula (I)

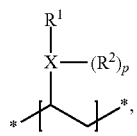
(I)

in which
X represents nitrogen or oxygen and
R¹ and R² in each case independently of one another represent hydrogen or a C2-C10 acyl group or R¹ and R² together with X form a five-membered or six-membered, saturated or unsaturated ring which optionally includes further heteroatoms selected from N and O, and/or is optionally substituted with at least one C1-C6 alkyl group and/or with at least one functional group, and
p=0 when X represents oxygen and p=1 when X represents nitrogen, the polymer A including no permanently ionic constituent units, d) at least one alkalizing agent, selected from ammonium hydroxide, monoethanolamine and sodium silicates, and mixtures thereof,
e) water, and
f) optionally at least one oxidation dye precursor and/or at least one substantive dye,
II. providing a composition (C), including
g) at least one peroxide compound,
III. mixing compositions (AB) and (C) with one another, then immediately
IV. applying the mixture of (AB) and (C) to the keratin fibers, and
V. rinsing out after a leave-in time of 0.1 to 60 minutes,
VI. optionally performing further styling, conditioning and/or drying treatments.

17. The method according to claim 13, wherein the at least one saturated dicarboxylic acid having 2 to 10 carbon atoms is selected from succinic acid and malic acid.

18. The method according to claim 16, wherein the at least one saturated dicarboxylic acid having 2 to 10 carbon atoms is selected from succinic acid and malic acid.

19. The coloring or bleaching agent according claim 10, wherein the at least one polymer (A) which has at least ten constituent units of formula (I) and which includes no permanently ionic constituent units is selected from the group consisting of polyvinylpyrrolidone, polyvinyl alcohol and mixtures thereof.

20. The method according claim 12, wherein the at least one polymer (A) which has at least ten constituent units of formula (I) and which includes no permanently ionic constituent units is selected from the group consisting of polyvinylpyrrolidone, polyvinyl alcohol and mixtures thereof.

21. The composition according claim 13, wherein the at least one polymer (A) which has at least ten constituent units of formula (I) and which includes no permanently ionic constituent units is selected from the group consisting of polyvinylpyrrolidone, polyvinyl alcohol and mixtures thereof.

* * * * *